United States Patent [19]

Haviv et al.

[11] 4,045,438

[45] Aug. 30, 1977

[54] CEPHALOSPORIN ANTIBIOTICS

[75] Inventors: Fortuna Haviv, Montreal, Canada; Abraham Patchornik, Ness-Ziona, Israel

[73] Assignee: Yeda Research and Development Co. Ltd., Rehovot, Israel

[21] Appl. No.: 625,558

[22] Filed: Oct. 24, 1975

[51] Int. Cl.$^2$ ............... C07D 501/22; C07D 501/30; C07D 501/32

[52] U.S. Cl. .................................. 544/29; 260/470; 260/471 R; 260/471 A; 260/473 R; 260/561 R; 260/332.2 A; 544/21; 544/26; 544/27; 544/28; 544/30; 424/246

[58] Field of Search ................................ 260/243 C

[56] References Cited

U.S. PATENT DOCUMENTS

| | | | |
|---|---|---|---|
| 3,341,531 | 9/1967 | Lewis et al. | 260/243 C |
| 3,812,116 | 5/1974 | Takano et al. | 260/243 C |
| 3,865,820 | 2/1975 | Schorr et al. | 260/243 C |
| 3,919,206 | 11/1975 | Patchornik et al. | 260/243 C |
| 3,920,640 | 11/1975 | Schorr et al. | 260/243 C |

*Primary Examiner*—Donald G. Daus
*Assistant Examiner*—David E. Wheeler
*Attorney, Agent, or Firm*—L. Ruth Hattan; Eugene O. Retter; George W. Rauchfuss, Jr.

[57] ABSTRACT

Novel cephalosporin antibiotic derivatives.

32 Claims, No Drawings

CEPHALOSPORIN ANTIBIOTICS

FIELD OF INVENTION

This invention relates to novel cephalosporin derivatives useful as antibiotics and processes for their preparation.

SUMMARY OF INVENTION

Compounds of the following general Formula I are useful as antibiotic agents:

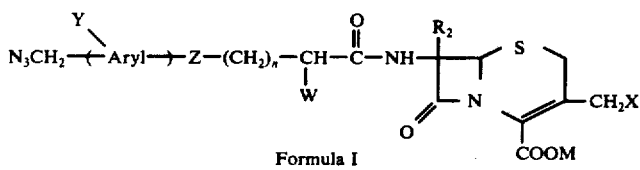

Formula I wherein Aryl is selected from phenyl and 2-thienyl; Y is selected from hydrogen, chlorine, bromine, a straight or branched lower alkyl group of from 1 to 4 carbon atoms and a lower alkoxy group of from 1 to 4 carbon atoms with the proviso that when Aryl is 2-thienyl, Y is hydrogen; Z is selected from a bond, oxygen, sulfur and imino with the proviso that when Aryl is 2-thienyl, Z is a bond; W is selected from hydrogen, methyl, amino, hydroxy, $SO_3H$, and $COOR_1$ wherein $R_1$ is selected from hydrogen and 5-indanyl; $n$ is zero, 1 or 2 with the proviso that when W is other than hydrogen or methyl and Z is other than a bond, $n$ is not zero; $R_2$ is selected from hydrogen and methoxy; M is selected from hydrogen; a pharmaceutically acceptable non-toxic cation; alkanoyloxymethyl wherein the alkanoyl moiety contains from 1 to 5 carbon atoms and may be straight or branched; alkanoylaminomethyl wherein the alkanoyl moiety contains from 1 to 5 carbon atoms and may be straight or branched and wherein the amino nitrogen atom may be substituted with an alkyl group of from 1 to 4 carbon atoms; alkoxycarbonylaminomethyl wherein the alkoxy moiety contains from 1 to 4 carbon atoms and may be straight or branched and wherein the amino nitrogen atom may be substituted with an alkyl group of from 1 to 4 carbon atoms; p-(alkanoyloxy)benzyl wherein the alkanoyl moiety contains from 1 to 5 carbon atoms and may be straight or branched; and aminoalkanoyloxymethyl wherein the alkanoyl moiety contains from 2 to 15 carbon atoms and the amino nitrogen may be mono- or di-substituted with a lower alkyl group of from 1 to 4 carbon atoms; X is selected from hydrogen, acetoxy, 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, 2-methyl-1,3,4-thiadiazol-5-ylthio and 1,2,3-triazol-5-ylthio; and pharmaceutically acceptable salts and individual optical isomers thereof.

DETAILED DESCRIPTION OF INVENTION

In general Formula I the substituent group as represented by M in addition to being hyrogen or a pharmaceutically acceptable non-toxic cation may also be alkanoyloxymethyl as represented by the structure:

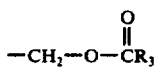

wherein $R_3$ is a straight or branched lower alkyl group of from 1 to 4 carbon atoms; alkanoylaminomethyl or alkoxycarbonylaminomethyl as represented by the structure:

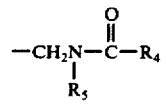

wherein $R_4$ is selected from a straight or branched lower alkyl group of from 1 to 4 carbon atoms and a straight or branched alkoxy group of from 1 to 4 carbon atoms and $R_5$ is selected from hydrogen and a lower alkyl group of from 1 to 4 carbon atoms; p-(alkanoyloxy)benzyl as represented by the structure:

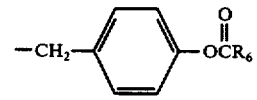

wherein $R_6$ is a straight or branched lower alkyl of from 1 to 4 carbon atoms, and aminoalkanoyloxymethyl as represented by the group:

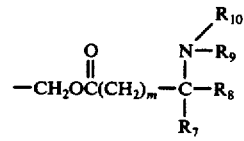

wherein $m$ is 0 to 5, each of $R_7$ and $R_8$ is selected from hydrogen and lower alkyl of from 1 to 4 carbon atoms, and each of $R_9$ and $R_{10}$ is selected from hydrogen and a straight or branched lower alkyl group of from 1 to 4 carbon atoms.

Illustrative examples of straight or branched lower alkyl groups of from 1 to 4 carbon atoms which Y, $R_3$, $R_4$, $R_6$, $R_9$ and $R_{10}$ may represent are methyl, ethyl, n-propyl, isopropyl, n-butyl and tert-butyl.

Examples of lower alkyl groups of from 1 to 4 carbon atoms which $R_5$, $R_7$ and $R_8$ may represent are methyl, ethyl, n-propyl and n-butyl.

Examples of lower alkoxy groups which Y may represent are methoxy, ethoxy, n-propoxy and n-butoxy.

Illustrative examples of straight or branched lower alkoxy groups which $R_4$ may represent are methoxy, ethoxy, n-propoxy, isopropoxy, sec-butoxy, and n-butoxy.

In general Formula I, the substituent group X may represent in addition to hydrogen and acetoxy, a heterocyclicthio group selected from 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, 2-methyl 1,3,4-thiadiazol-5-ylthio or b 1,2,3-triazol-5-ylthio as represented by the following respective structures:

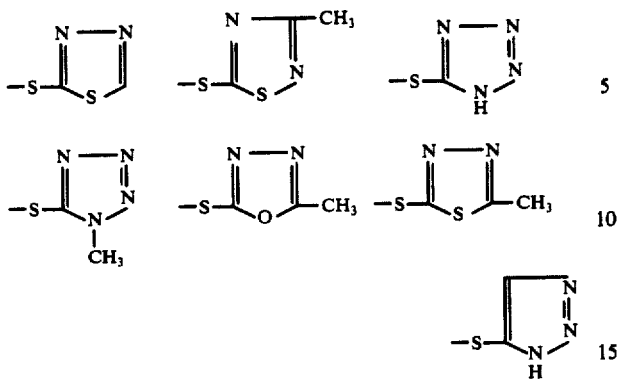

When the Aryl group in the compounds of general Formula I represents phenyl, each of the azidomethyl substituent and the Y substituent may be individually attached to any of the positions 2 through 6 of the phenyl ring. Compounds of this type may be represented by the following general Formula II.

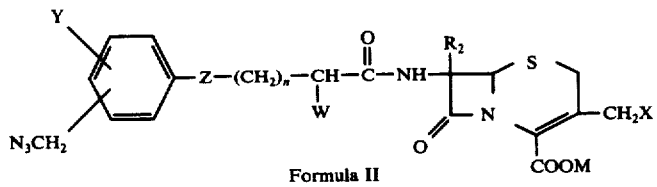

Formula II

The preferred positions of the attachments of the azidomethyl substituent in the above Formula II are the ortho- and para- positions of the phenyl ring. In the above Formula II, the substituents as represented by Y, Z, n, W, $R_2$, M and X have the meanings defined in general Formula I.

When the Aryl group in the compounds of general Formula I represent 2-thienyl, Y is hydrogen, and Z is a bond. Compounds of this type may be represented by the following Formula III.

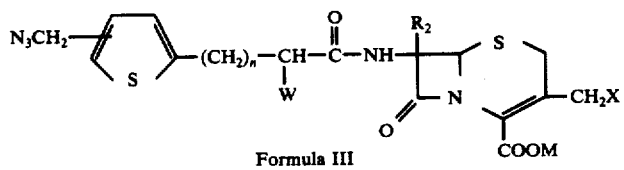

Formula III

In the compounds of the above Formula III, the azidomethyl substituent may be attached at the 4 or 5 positions of the thienyl group. In the above Formula III, the substituents as represented by n, W, $R_2$, M and X have the meanings defined in general Formula I.

In the compounds of general Formulas I to III, it is apparent that the $R_2$ substituent may be either cis or trans to the hydrogen atom at the 6- position of the cephalosporin derivatives. The compounds of Formulas I to III wherein the $R_2$ substituent is in the cis position to the aforementioned hydrogen atoms are preferred.

Other preferred embodiments of this invention are:
A. compounds wherein W represents hydrogen, hydroxy, amino, $SO_3H$, and $COOR_1$ wherein $R_1$ represents hydrogen in that such substitution results in compounds having broader spectrum activity and/or improved oral activity for example wherein:

1. W represents hydroxy are more resistant to β-lactamase organisms;
2. W represents $SO_3H$ or $COOR_1$ wherein $R_1$ represents hydrogen have broader gram negative spectrum;
3. W represents $NH_2$ have improved oral activity;

B. compounds wherein $R_2$ represents methoxy are of particular interest in that such compounds demonstrate antibacterial activity against cephalosphorinase producing gram negative organisms.
C. compounds wherein X represents acetoxy, 2-methyl-1,3,4-thiadiazol-5-ylthio, or 1-methyltetrazol-5-ylthio. Of the preferred embodiments set forth in (A), (B) and
C. compounds wherein Z represents a bond are more preferred.

The most preferred compounds of this invention are those represented by the following Formula IV:

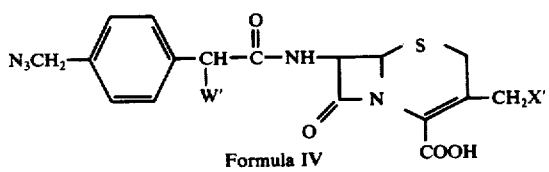

Formula IV wherein W' is selected from hydrogen, hydroxy, amino, COOH or $SO_3H$; X' is selected from hydrogen, acetoxy, 2-methyl-1,3,4-thiadiazol-5-ylthio or 1-methyltetrazol-5-ylthio; and pharmaceutically acceptable salts thereof.

In the above Formula IV, compounds wherein the hydrogen atoms at the 6- and 7- positions are cis to one another are preferred.

The individual optical isomers of the compounds of this invention wherein W or W' is other than hydrogen are also included within the scope of this invention.

The non-toxic acid addition salts of the compounds of this invention such as mineral acid addition salts, for example, hydrogen chloride, hydrogen bromide, hydrogen iodide, sulfates, sulfamate, and phosphate, an organic acid addition salt, for example, maleate, acetate, citrate, oxalate, succinate, benzoate, tartrate, fumarate, malate, mandelate, and ascorbate, are also included within the scope of this invention.

Also within the scope of this invention are the non-toxic pharmaceutically acceptable salts of the compounds of this invention wherein W represents COOH or $SO_3H$ and compounds wherein M represents hydrogen. Illustrative pharmaceutically acceptable salts of these acid derivatives are primary, secondary, or tertiary amines, for example, cyclohexylamine, ethylamine and pyridine.

The pharmaceutically acceptable cations which may be present as the group M in the compounds of general Formulas I to III include alkali metal ions, for example, sodium ion, potassium ion, calcium ion as well as ammonium, and organic amine cations, for example, lower alkyl ammonium groups, such as triethylammonium, and N-ethylpiperidine.

The salt forms of compounds of Formulas I to III wherein M is a pharmaceutically acceptable cation are prepared in the manner recognized in the art and may be formed in situ or by reacting the corresponding acid with base, for example, sodium bicarbonate or triethylamine.

The compounds of this invention may be administered in a manner similar to that of many well-known cephalosporin compounds, for example, cephalexin, cephalothin, or cephaloglycine. They may be administered alone or in the form of pharmaceutical preparations either orally or parenterally and topically to warm blooded animals, that is, birds, and mammals, for example, cats, dogs, cows, sheep and horses, and humans. For oral administration, the compounds may be administered in the form of tablets, capsules or pills or in the form of elixirs or suspensions. For parenteral adminstration, they are best used in the form of a sterile aqueous solution which may contain other solutes, for example enough saline or glucose to make the solution isotonic. For topical administration, the compounds may be incorporated in creams or ointments.

Illustrative examples of bacteria against which the compounds of this invention are active are *Staphylococcus aureus, Salmonella schottmuelleri, Klebsiella pneumoniae, Diplococcus pneumoniae,* and *Streptococcus pyogenes.*

An illustrative example of a cephalosporin derivative of this invention is 3-[(acetyloxy)methyl]-7-[[2-[4-(azidomethyl)phenyl]acetyl]amino]-8-oxo-5-thia-1-azabicyclo[4.2.0]-oct-2-ene-2-carboxylic acid. Additional examples of compounds of this invention are set forth hereinbelow in the specific examples which are representative of the invention.

The compounds of this invention wherein $R_1$ is hydrogen are prepared by coupling 7-aminocephalosporanic acid or a derivative thereof having the formula:

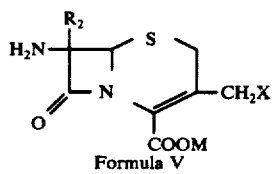

Formula V wherein $R_2$, M, and X have the meanings defined in general Formula I with an acid of the following Formula VI or a functional derivative thereof:

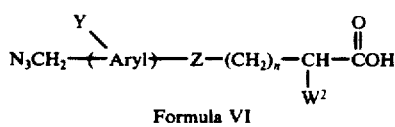

Formula VI wherein Aryl, Y, Z, and n have the meanings defined in general Formula I, and $W_2$ is selected from hydrogen, methyl, amino, hydroxy, $SO_3H$, and COOH. When the substituent group $W_2$ in the above Formula IV represents an amino group, suitable blocking groups, for example, an acid salt such as hydrochloride salt, an acyl group, or tert-butoxycarbonyl may be employed to protect the amino function. Such blocking groups are removed after the coupling reaction by methods generally known in the art, for example, as described by Lemieux et al., in U.S. Pat. No. 3,657,232.

Functional equivalents of the acids as represented by Formula IV include the acid halides, for example, the acid chloride, acid anhydrides, including mixed anhydrides with, for example, alkylphosphoric acids, lower aliphatic monoesters of carbonic acid, or alkyl or aryl sulfonic acids. Additionally, the acid azide or an active ester or thioester for example, with p-nitrophenol, 2,4-dinitrophenol, or thioacetic acid, may be used or the free acid as represented by Formula VI may be coupled with the 7-aminocephalosporanic acid derivative as represented by Formula V after first reacting the acid with N,N'-dimethylchloroforminium chloride or by use of a carbodiimide reagent, for example, N,N'-diisopropylcarbodiimide, N,N'-dicyclohexylcarbodiimide, or N-cyclohexyl-N'-(2-morpholinoethyl)carbodiimide.

The coupling reaction is generally carried out in the presence of a solvent. Suitable solvents include ethyl acetate, acetone, dioxane, acetonitrile, chloroform, ethylene chloride, tetrahydrofuran and dimethylformamide. As hydrophilic solvents are employed mixtures of these solvents with water are also suitable for the above reaction. The coupling reaction is generally carried out in the presence of a base, for example, an alkaline bicarbonate. The temperature of the reaction may vary from − 10° to 100° C, and the reaction time may vary from about ½ to 10 hours. The cephalosporin products are isolated by conventional methods.

Compounds of Formula V wherein $R_2$ is hydrogen, M is hydrogen, or a pharmaceutically acceptable non-toxic cation, and X is hydrogen or acetoxy are commercially available or may be prepared by methods well-known in the art. The corresponding compounds wherein $R_2$ is methoxy may be prepared by the general procedures described in U.S. Pat. No. 3,778,432.

Compounds of Formula V wherein M is alkanoyloxymethyl may be prepared by reacting the corresponding acid in the form of a salt, such as, an alkali metal salt or the triethylammonium salt with a compound of the formula:

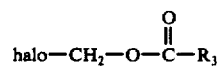

wherein halo is chlorine or bromine, and $R_3$ is a straight or branched lower alkyl group of from 1 to 4 carbon atoms by the general procedure desribed in U.S. Pat. No. 3,655,658.

Compounds of Formula V wherein M is alkanoylaminomethyl or alkoxycarbonylaminomethyl are prepared by treating the sodium salt of acid derivatives of Formula V in an organic solvent such as dimethylformamide or hexamethylphosphoramide, at room temperature with an equivalent amount of an alkanoylaminomethyl halide or an alkoxycarbonylaminomethyl halide for ½ to 3 hours after which the mixture is poured into ice water. The resulting precipitated product is isolated by standard procedures.

Compounds of Formula V wherein M is p-(alkanoyloxy)benzyl are prepared by adding two equivalents of the p-(alkanoyloxy)benzyl alcohol to a suspension of the sodium salt of acid derivatives of Formula V in dimethylformamide or hexamethylphosphoramide after which the mixture is cooled to 0° C. 1.2 equivalents of dicyclohexylcarbodiimide and dimethylformamide are added dropwise to the mixture with stirring. The mixture is stirred at 0° C for ¼ to 3 hours and then an additional 2 to 5 hours at room temperature. The formed dicyclohexylurea is removed by filtration and the filtrate is diluted with chloroform, methylene chloride, or ethylacetate, washed with water and dried to give the product.

Compounds of Formula V wherein M is aminoalkanoyloxymethyl are prepared by mixing a suspension of the sodium salt of an acid of Formula V and an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethylacetate or methylene chloride washed with water, aqueous base, then water. The organic phase is separated and the precipitate isolated by conventional means followed by deprotection of the amine group to give the product.

Compounds of Formula V wherein X is a heterocyclic thio group as described in Formula I are prepared by dissolving 1 equivalent of the acid in the form of a salt, such as, the sodium salt wherein X is acetoxy in about 500 to 200 ml of water at a temperature of from 50° to 80° C under a nitrogen atmosphere and subsequently adding 1 equivalent of a base, such as, triethylammonium or sodium bicarbonate and 1 to 3 equivalents of an appropriate heterocyclic-thiol selected from a compound having the following structure:

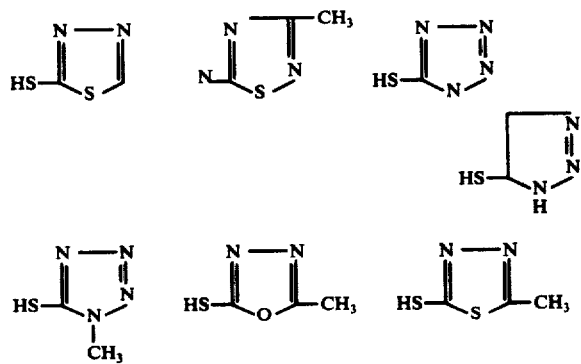

Compounds of general Formula VI are prepared by treating a compound of the following formula:

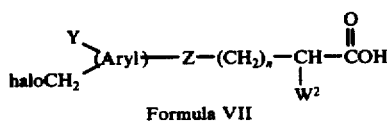

Formula VII wherein halo is chlorine or bromine, and Aryl, Y, Z, n, and W² have the meanings defined in general Formula VI with sodium azide or potassium azide in a solvent, such as, a lower alcohol, for example, methanol, ethanol, isopropyl alcohol or n-butanol, or dimethylsulfoxide, dimethylformamide or aqueous mixtures of these solvents, for from ½ hour to 24 hours at a temperature range from 0° to 125° C. The products can be isolated by conventional procedures. In some instances it may be more convenient to convert the acid as represented by Formula VII to the corresponding methyl ester by, for example, treating the acid with diazomethane at −10° C then stirring the mixture for about 10 to 30 minutes at room temperature.

When the substituent group W² in compounds of general Formula VII represents amino, the amino group is protected by a suitable blocking group, for example, tert-butoxycarbonyl prior to the treatment with sodium azide or potassium azide. The blocking group may be removed after the coupling reaction by a mild acid hydrolysis or hydrogenolysis by procedures known in the art.

The compounds of Formula VII are prepared by direct halomethylation as described hereinbelow of an acid of the formula:

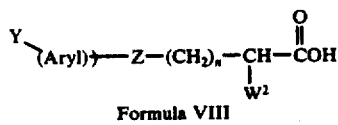

Formula VIII wherein Aryl, Y, Z, n and W² have the meanings defined in general Formula VI which are commercially available or are obtained by methods well-known in the art.

When the substituent group W₂ in the compounds of Formula VIII represents amino, the amino group is protected by a suitable blocking group as for example described hereinabove in reference to compounds of general Formula VII.

The halomethylated derivatives of the compounds of Formula VIII are obtained by several methods. For example, a compound of Formula VIII with a source of formaldehyde such as paraformaldehyde, $ClCH_2OCH_3$, or formalin solution, in the presence of a Lewis acid, such as $ZnCl_2$, $AlCl_3$, $SnCl_4$ or $ClSO_3H$ in a solvent, such as, petroleum ether, chloroform, carbon tetrachloride or benzene at a temperature ranging from −10° to 100° C during which time hydrogen chloride gas or hydrogen bromide gas is bubbled into the reaction mixture, will give compounds of general Formula VII.

The reaction of an acid of Formula VIII with 34–38% formalin in concentrated hydrochloric acid at temperatures ranging from −10° to 100° C during which time hydrogen chloroide gas or hydrogen bromide gas is bubbled through the reaction mixture also yields compounds of the general Formula VII.

Additionally, upon reaction of an acid of Formula VIII with trioxane in acetic acid or phosphoric acid at temperatures of from −10° to 100° C during which time hydrogen bromide or hydrogen chloride gas is bubbled through the reaction mixture, compounds of general Formula VII are obained. Or, the reaction of an acid of Formula VIII in the presence of a Lewis acid, such as, those described hereinabove, with chloromethyl ether at temperatures from −10° to 100° C or the reaction of the acid in acetic acid or concentrated sulfuric acid with dichloromethyl ether in the presence of zinc chloride will give compounds of general Formula VII.

The compounds of Formula VII wherein W² represents COOH, and Aryl is phenyl are preferably obtained by treating the corresponding diethyl ester of Formula VIII with 40% formalin in the presence of anydrous zinc chloride or hydrogen bromide gas is bubbled into the reaction mixture followed by acid hydrolysis.

Compounds of Formula VII wherein $W^2$ represents $SO_3H$ may be obtained by the halomethylation reactions described above using an acid of Formula VIII wherein $W^2$ represents $SO_3H$ or the carboxymethyl ester thereof, in which latter case the resulting halomethylated compound is converted to the free COOH by acid hydrolysis.

In the halomethylation of compounds of Formula VIII wherein $W^2$ represents OH it may be advantageous to protect the OH group prior to halomethylation as described by V. Reichert, et. al., Pharmazie 5, 10 (1950).

Compounds of this invention wherein $R_1$ is 5-indanyl are prepared by reacting the corresponding acid, that is, compounds of general Formula I wherein $R_1$ is hydrogen with 5-indanol in an inert solvent in the presence of N,N'-dicylohexylcarbodiimide at a pH of about 2.5 and a temperature of from 20° to 30° C. Equimolar amounts of the reactants are employed or a slight excess of the 5-indanyl may be used. The molar amount of N,N'-dicyclohexylcarbodiimide employed is equivalent to the molar amount of 5-indanol. Suitable solvents for the reaction are dioxane, tetrahydrofuran, ethyl acetate, dimethylformamide and methylene chloride.

The compounds of this invention may also be prepared by linking a modified polystyrene containing nitrophenol or hydroxysuccinimide groups with an acid of general Formula VI by the general procedure described in Canadian Pat. No. 892,580 issued Feb. 8, 1972, by substituting a compound of general Formula V for the penicillanic acid derivatives described therein.

Additionally, the compounds of this invention wherein X represents a heterocyclicthio group selected from 1,3,4-thiadiazol-5-ylthio, 3-methyl-1,2,3-thiadiazol-5-ylthio, tetrazol-5-ylthio, 1-methyltetrazol-5-ylthio, 2-methyl-1,3,4-oxadiazol-5-ylthio, or 2-methyl-1,3,4-thiadiazol-5-ylthio 1,2,3-triazol-5-ylthio and M represents hydrogen may be prepared by reacting the 3-[(acetyloxy)methyl]-derivative with the appropriate heterocyclicthiol group as represented by the following:

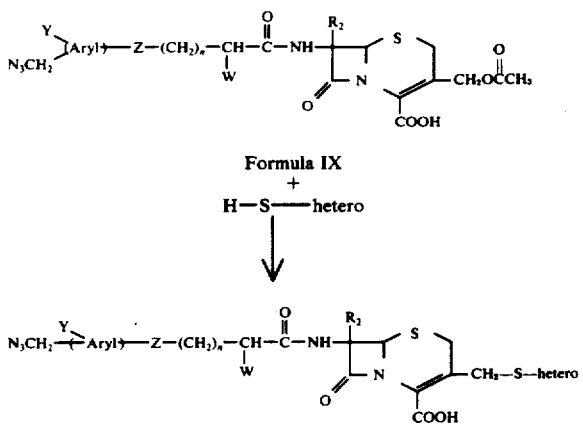

Formula IX

In the above Formula IX and X the substituents groups Aryl, Y, Z, n, W and $R_2$ have the meanings defined in general Formula I, and the moiety S-hetero is selected from 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, 2-methyl-1,3,4-thiadiazol-5-ylthio, or 1,2,3-triazol-5-ylthio.

In the above reaction one equivalent of the sodium salt derivative is dissolved in water at a temperature of from 25° to 90° C under a nitrogen atmosphere followed by the addition of 1 equivalent of a base such as triethylamine or sodium bicarbonate and from 1 to 3 equivalents of the heterothiol derivative after which the reaction mixture is filtered for about 2 to 6 hours at a temperature of from 25° to 90° C.

Compounds of this invention wherein M represents alkanoylaminomethyl or alkoxycarbonylaminomethyl, and W is other than COOH may also be prepared by reacting the corresponding acid in the form of a salt such as an alkali metal salt, for example, the sodium salt with 1.5 to 2.5 equivalents of an appropriate alkanoylaminomethyl halide or alkoxycarbonylaminomethyl halide each of which may be represented by the structure:

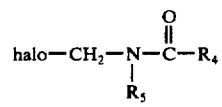

wherein halo is selected from a reactive halogen atom such as chlorine or bromine, $R_4$ is selected from a straight or branched lower alkyl group of from 1 to 4 carbon atoms or a straight or branched lower alkoxy group of from 1 to 4 carbon atoms, and $R_5$ is hydrogen or a lower alkyl group of from 1 to 4 carbon atoms. The reactants are stirred for about 1 to 5 hours in dimethylformamide, hexamethylphosphoramide or a similar solvent at a temperature ranging from 10° to 45° C after which the reaction mixture is poured into ice water and decanted. The oily residue is taken up in an organic solvent such as ethylacetate, methylene chloride or benzene, washed with base then with water and dried over magnesium sulfate. The organic solution is evaporated to dryness in vacuo to give the desired ester.

Prior to the above esterification reaction, compounds wherein W represents amino are protected with blocking groups for example, tert-butoxycarbonyl or carbobenzyloxy, such groups being removed on completion of the esterification procedure by methods generally known in the art, for example, by the methods set forth in the aforementioned U.S. Pat. No. 3,657,232.

Compounds of this invention wherein M represents p-(alkanoyloxy)benzyl, and W is other than COOH may also be prepared by reacting molar equivalents of the corresponding acid and p-(alkanoyloxy)benzyl alcohol wherein the alkanoyl moiety contains from 1 to 4 carbon atoms and may be straight or branched. The reactants are dissolved in an organic solvent such as dimethylformamide or hexamethylphosformide and cooled to a temperature of from $-15°$ to 25° C after which an equivalent quantity of dicyclohexylcarbodiimide in dimethylformamide or hexamethylphosphoramide is added dropwise to the reaction mixture with stirring. Stirring is continued for ½ to 2 hours at temperatures of from $-15°$ to 25° C and then 4 to 6 hours at from 25° to 45° C. The formed dicyclohexylurea is removed by filtration, and the filtrate is diluted with chloroform, ethylacetate or methylene chloride and washed with water. The organic layer is dried and evaporated to give the product.

Compounds of this invention wherein M is alkanoyloxymethyl, and W is other than COOH may also be prepared by reacting the corresponding acid in the form of a salt, such as, an alkali metal salt or the triethylammonium salt with a compound of the formula:

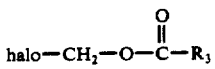

wherein halo is chlorine or bromine, and $R_3$ is a straight or branched lower alkyl group of from 1 to 4 carbon atoms by the general procedure described in U.S. Pat. No. 3,655,658.

Compounds of this invention wherein M is aminoalkanoyloxymethyl, and W is other than COOH may also be prepared by mixing a suspension of the sodium salt of the corresponding acid and an excess of an appropriate amine protected aminoalkanoyloxymethyl halide in a solvent such as dimethylformamide, hexamethylphosphoramide or dimethylsulfoxide for 2 to 96 hours. The mixture is then diluted with a solvent such as ethylacetate or methylene chloride, washed with water, aqueous base, then water. The organic phase is separated and the precipitate isolated by conventional means followed by deprotection of the amine group to give the product.

Compounds of this invention wherein $R_1$ is hydrogen may also be prepared by solvolysis of a compound of the formula

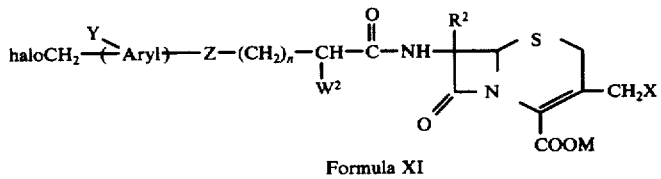

Formula XI wherein Aryl, Y, Z, $n$, $R^2$, M and X have the meanings defined in general Formula I; halo is chlorine or bromine, and $W^2$ is hydrogen, methyl, amino, hydroxy, $SO_3H$ or COOH; with sodium azide or potassium azide in a solvent, such as, a lower alcohol, for example, methanol, ethanol, isopropyl alcohol, n-butanol or dimethylsulfoxide, dimethylformamide or aqueous mixtures of these solvents. The reaction is carried out for from ½ hour to 24 hours at a temperature of from 0° to 125° C. The products are isolated by conventional means.

Compounds of Formula IX are obtained by coupling a compound of Formula VII or a reactive derivative thereof with a compound of Formula V by conventional procedures.

The following specific examples are illustrative of the compounds of the invention and methods of preparing the compounds.

EXAMPLE 1 p-Chloromethylphenylacetyl chloride

A. At a temperature of from −10° to 0° C hydrogen chloride gas is bubbled through a stirred mixture of 102 g of phenylacetic acid, 67.5 g of paraformaldehyde and 67.5 g of zinc chloride in 1000 ml of petroleum ether for 1 hour. Stirring is continued for about one hour at room temperature after which the mixture is refluxed for about 2 hours during which time hydrogen chloride gas is bubbled into the mixture. To the reaction mixture is added 1000 ml each of methylene chloride and water. The organic phase is separated and the aqueous phase is extracted twice with methylene chloride. The combined organic phases are extracted four times with a saturated sodium bicarbonate solution. The organic neutral phase is dried over anhydrous sodium sulfate, filtered and the solvent is removed under vacuum to give a neutral by-product which is further identified in Example 5 below. The basic aqueous phase is separated an acidified with cold concentrated hydrochloric acid to pH 2–3, then extracted three times with methylene chloride. The methylene chloride fraction is dried over anhydrous sodium sulfate, filtered and the solvent evaporated. The resulting oily acidic product is chromatographed on silica gel using benzene and benzene-acetone as the eluant to give p-chloromethylphenylacetic acid which is recrystallized from hot chloroform. M.P. 147°–149° C.

B. A mixture of 1 g of p-chloromethylphenylacetic acid and 6 ml of thionyl chloride is stirred at room temperature for 25 hours after which the excess thionyl chloride is removed under vacuum to yield p-chloromethylphenylacetyl chloride.

When in Example 1 (A) an acid selected from Table I is substituted for phenylacetic acid the respective chloromethyl derivative listed in Table I is obtained which can be converted to the acid chloride by the procedure of Example 1 (B).

TABLE I

| Acid | Chloromethyl derivative |
| --- | --- |
| hydrotropic acid | p-chloromethylhydrotropic acid |
| mandelic acid | p-chloromethylmandelic acid |
| dihydrocinnamic acid | p-chloromethyldihydrocinnamic acid |
| 2-methylhydrocinnamic acid | p-chloromethyl-2-methylhydrocinnamic acid |
| 3-phenyllactic acid | 3-(p-chloromethylphenyl)-lactic acid |
| 4-phenylbutyric acid | 4-(p-chloromethylphenyl)-butyric acid |
| 2-methyl-4-phenyl-butyric acid | 2-methyl-4-(p-chloromethylphenyl)butyric acid |
| 2-hydroxy-4-phenyl-butyric acid | 2-hydroxy-4-(p-chloromethylphenyl)butyric acid |
| phenoxyacetic acid | p-chloromethylphenoxyacetic acid |
| 2-phenoxypropionic acid | 2-(p-chloromethylphenoxy)-propionic acid |
| 4-phenoxybutyric acid | 4-(p-chloromethylphenoxy)-butyric acid |
| 2-methyl-4-phenoxybutyric acid | 2-methyl-4-(p-chloromethylphenoxy)butyric acid |
| 3-phenoxypropionic acid | 3-(p-chloromethylphenoxy)-propionic acid |
| 3-phenoxylactic acid | 3-(p-chloromethylphenoxy)lactic acid |
| anilinoacetic acid | p-chloromethylanilino acetic acid |
| 2-hydroxy-2-(2-thienyl)acetic acid | 2-hydroxy-2-[2-(5-chloromethyl)thienyl]acetic acid |
| 2-anilinopropionic | 2-(p-chloromethyl)anilinopropionic acid |
| 4-anilinobutyric acid | 4-(p-chloromethylanilino)-butyric acid |
| 3-anilinobutyric acid | 3-(p-chloromethylanilino)-butyric acid |
| phenylthioacetic acid | p-chloromethylphenylthioacetic acid |
| 2-phenylthiopropionic acid | 2-(p-chloromethylphenyl)-thiopropionic acid |
| 4-phenylthiobutyric acid | 4-(p-chloromethylphenyl)-thiobutyric acid |
| o-chlorophenylacetic acid | o-chloro-p-chloromethylphenylacetic acid |

EXAMPLE 2 p-chloromethylphenylglycine

A mixture of 2.03 g of trifluoroacetylated phenylglycine, 0.8 g of zinc chloride in chloromethylether is heated at 65° C for 12 hours. The excess reagent is removed under vacuum, and the residue is dissolved in $CH_2Cl_2$, washed with saturated $NaHCO_3$ solution then saturated sodium chloride solution. The neutral organic phase is dried over $Na_2SO_4$ and concentrated to an oil which was purified by column chromatography yielding the methyl ester of p-chloromethylphenylglycine which upon hydrolysis using aqueous hydrochloric acid gives the acid hydrochloride. The acid hydrochloride is converted to the free acid by adjusting the pH of the aqueous solution to about 5. Similarly, the chloromethyl derivatives listed in Table II may be prepared from the listed acid.

TABLE II

| Acid | Chloromethyl derivative |
|---|---|
| phenylalanine | p-(chloromethylphenyl)-alanine |
| 2-amino-4-phenyl-butyric acid | 2-amino-4-(p-chloromethylphenyl)butyric acid |
| 2-amino-4-phenoxy-butyric acid | 2-amino-4-(p-chloromethylphenoxy)butyric acid |
| 3-phenoxyalanine | 3-(p-chloromethylphenoxy)alanine |
| 2-amino-4-anilino-butyric acid | 2-amino-4-(p-chloromethylanilino)butyric acid |
| 2-amino-4-phenyl-thiobutyric acid | 2-amino-4-(p-chloromethylphenyl)thiobutyric acid |
| 3-phenylthioalanine | 3-(p-chloromethylphenyl)thioalanine |
| 2-(2-thienyl)glycine | 2-[2-(5-chloromethyl)-thienyl]glycine |
| 2-amino-3-(2-thienyl)-propionic acid | 2-amino-3-[2-(5-chloromethyl)thienyl]propionic acid |
| 2-amino-4-(2-thienyl)-butyric acid | 2-amino-4-[2-(5-chloromethyl)thienyl]butyric acid |

EXAMPLE 3 p-Chloromethylphenylmalonic acid

When in the procedure of Example 1 (A) an equivalent amount of phenylmalonic acid diethyl ester is substituted for phenylacetic acid, p-chloromethylphenylmalonic acid diethyl ester is obtained which yields the corresponding acid upon acid hydrolysis. In a similar manner the chloromethyl derivatives listed in Table III may be prepared when the diethyl ester of the corresponding acid listed in Table III is substituted for phenylmalonic acid diethyl ester.

TABLE III

| Acid | Chloromethyl derivative |
|---|---|
| 2-sulfophenylacetic acid | 2-sulfo-p-chloromethylphenylacetic acid |
| 3-phenyl-2-sulfopropionic acid | 3-(p-chloromethylphenyl)-2-sulfopropionic acid |
| 4-phenyl-2-sulfobutyric acid | 4-(p-chloromethylphenyl)-2-sulfobutyric acid |
| benzylmalonic acid | p-chloromethylbenzylmalonic acid |
| phenethylmalonic acid | p-chloromethylphenethylmalonic acid |
| 2-phenoxyethyl-malonic acid | 2-(p-chloromethylphenoxy)ethylmalonic acid |
| 2-phenylthioethyl-malonic acid | 2-(p-chloromethylphenyl)thioethyl-malonic acid |
| anilinomethyl-malonic acid | p-chloromethylanilino-methylmalonic acid |
| 2-thienylmalonic acid | 2-[2-(5-chloromethyl)-thienyl]malonic acid |
| 2-thenylmalonic acid | 2-[2-(5-chloromethyl)-thenyl]malonic acid |

EXAMPE 4

5-Chloromethyl-2-thienylacetyl chloride

2-Thiophenecarboxylic acid is treated in a solution of chloroform with chloromethyl ether in the presence of 0.9 to 2.2 equivalents of aluminum chloride to give 5-chloromethyl-2-thienylcarboxylic acid. Treatment of the obtained acid with excess thionyl chloride at room temperature for about 16 hours yields the acid chloride which is reacted with diazomethane to give the corresponding diazoketone. A methanol solution of the diazoketone is irradiated under nitrogen for about one hour with a high pressure mercury lamp using a Quarz filter. The methyl 5-chloromethyl-2-thienylacetate is obtained upon work up and column chromatography on silica gel. The acetate is hydrolyzed by treatment of a 1:1 mixture of acetic acid and concentrated hydrochloric acid at room temperature overnight to give 5-chloromethyl-2-thienylacetic acid.

When in the procedure of Example 1 (B) 5-chloromethyl-2-thienylacetic acid, is substituted for p-chloromethylphenyl acetic acid, 5-chloromethyl-2-thienylacetyl chloride is obtained.

EXAMPLE 5 o-Hydroxymethylphenylacetic acid lactone

The neutral by-product obtained in Example 1 is purified by sublimation under vacuum (0.05 mm Hg at 80° C) to give o-hydroxymethylphenylacetic acid lactone. M.P. 82° C.

EXAMPLE 6 o-Bromomethylphenylacetyl chloride

To a solution of 5 ml of glacial acetic acid saturated with hydrogen bromide gas is added at 0° C a solution of o-hydroxymethylphenylacetic acid lactone (0.55 g) in 2 ml of glacial acetic acid. The mixture is stirred at room temperature for 2 hours then refluxed for 1 hour during which time hydrogen bromide gas is bubbled into the mixture. The excess lactone and solvent are removed under high vacuum at room temperature. The resulting oily residue is triturated three times with hexane to give o-bromomethylphenylacetic acid. M.P. 110° C.

A solution of 0.18 g of o-bromomethylphenylacetic acid in excess thionyl chloride is stirred at room temperature for 18 hours after which the unreacted thionyl chloride is removed under high vacuum to give o-bromomethylphenylacetyl chloride as an oily residue.

EXAMPLE 7 o-Chloromethyl-p-methoxymandelic acid chloride

A solution of 1.1 g of 2-chloromethyl-4-methoxymandelic acid, obtained by the procedure described by B. Reichert et al., Pharmazie 5,10 (1950), in 25 ml of thionyl chloride is stirred at room temperature for about 16 hours after which the excess thionyl chloride is removed under high vacuum to give o-chloromethyl-p-methoxymandelic acid chloride as an oil.

EXAMPLE 8

3-[(Acetyloxy)methyl]-7-amino-8-oxo-5-thia-1-azabicyclo[4.2.0]oct-2-ene-2-carboxylic acid pivalyloxymethyl ester To 35 ml of dimethyl formamide is added 7.5 g of the sodium salt of 3-[(acetyloxy)methyl]-7-amino-8-oxo-5-thia-1-azabicyclo[4.2.0 ]oct-2-ene-2-carboxylic acid, and the solution is stirred at room temperature for about 30 minutes after which 8 ml of chloromethylpivalate is added. Stirring is continued at room temperature for about 3 hours. The mixture is diluted with ethyl acetate and washed with water. The organic layer is separated and evaporated to dryness. The residue is recrystallized from ethyl acetate to give 3-[(acetyloxy)methyl]-7-amino-8-oxo-5-thia-1-azabicyclo[4.2.0]oct-2-ene2-carboxylic acid pivalyloxymethyl ester.

In a similar manner when an appropriate amount of chloromethylpropionate chloromethylacetate or chloromethylbutyrate is substituted for chloromethylpivalate, the following respective products are obtained:

3-[(acetyloxy)methyl]-7-amino-8-oxo-5-thia-1-azabicyclo [4.2.0]oct-2-ene-2-carboxylic acid propionyloxymethyl ester,
3-[(acetyloxy)methyl]-7-amino-8-oxo-5-thia-1-azabicyclo[4.2.0]oct-2-ene-2-carboxylic acid acetyloxymethyl ester,
3-[(acetyloxy)methyl]-7-amino-8-oxo-5-thia-1-azabicyclo[4.2.0]oct-2-ene-2-carboxylic acid butyryloxymethyl ester.

EXAMPLE 9

3-[(Acetyloxy)methyl]-7-amino-8-oxo-5-thia-1-azabicyclo[4.2.0]oct-2-ene-2-carboxylic acid 2-amino-3-methylbutyryloxymethyl ester A suspension of 5 grams of 3-[(acetyloxy)methyl]-7-amino-8-oxo-5-thia-1-azabicyclo[4.2.0]oct-2-ene-2-carboxylic acid sodium salt and 8.5 grams of N-tert-butoxycarbonyl-L-valine chloromethyl ester, which is prepared by the general procedure described in W. German Offen. No. 2,236,620, are mixed in 100 ml of dimethyl formamide and stirred for 71 hours. The mixture is diluted with ethyl acetate, washed with water with aqueous bicarbonate and again with water. The organic layer is dried over magnesium sulfate, filtered, and evaporated to dryness to give 3-[(acetyloxy)methyl]-7-amino-8-oxo-5-thia-1-azabicyclo[4.2.0]oct-2-ene- 2-carboxylic acid N-tert-butoxycarbonyl-2-amino-3-methylbutyryloxymethyl ester from which the amine protecting group is removed by standard procedures to give the title product.

EXAMPLE 10

3-[(Acetyloxy)methyl]-7-amino-8-oxo5-thia-1-azabicyclo[4.2.0]oct-2-ene-2-carboxylic acid N-ethoxycarbonyl-N-methylaminomethyl ester 725 mg (2.5 mM) of the sodium salt of 3-[(acetyloxy)methyl]- -7-amino-8-oxo-5-thia-1-azabicyclo[4.2.0]oct-2- ene-2-carboxylic acid in 50 ml of dimethyl formamide is treated at room temperature with 375 mg (2.5 mM) of N-chloromethyl-N-methylurethane for one hour. The mixture is carefully poured into ice water and the precipitated solid is removed by filtration and washed with water. The solid is dissolved in ethylacetate and washed with aqueous sodium bicarbonte and then with water. The organic layer is dried over magnesium sulfate filtered and evaporated to dryness in vacuo to give 3-[(acetyloxy)methyl]-7-amino- 8-oxo-5-thia-1-azabicyclo[4.2.0]oct-2-ene-2-carboxylic acid N-ethoxycarbonyl-N-methylaminomethyl ester.

When in the above procedure an appropriate amount of N-methyl-N-propionylaminomethyl chloride, N-butyrylaminomethyl chloride, N-acetylaminomethyl chloride, or N-methyl- N-ethoxycarbonylaminomethyl chloride is substituted for N-chloromethyl-N-methylurethane the following respective compounds are obtained:

3-[(acetyloxy)methyl]-7-amino-8-oxo-5-thia-1-azabicyclo[4.2.0]oct-2-ene-2-carboxylic acid N-methyl-N-propionylaminomethyl ester,
3-[(acetyloxy)methyl]-7-amino-8-oxo-5-this-1-azabicyclo[4.2.0]oct-2-ene-2-carboxylic acid N-butyrylaminomethyl ester,
3-[(acetyloxy)methyl]-7-amino-8-oxo-5-thia-1-azabicyclo[4.2.0]oct-2-ene-2-carboxylic acid N-acetylaminomethyl ester and,
3-[(acetyloxy)methyl]-7-amino-8-oxo-5-thia-1-azabicyclo[4.2.0]oct-2-ene-2-carboxylic acid N-methyl-N-ethoxycarbonylaminomethyl ester.

EXAMPLE 11

3-[(Acetyloxy)methyl]-7-amino-8-oxo-5-thia-1-azabicyclo[4.2.0]oct-2-ene-2-carboxylic acid p-pivalyloxybenzyl ester To a suspension of 6.6 mM of 3-[(acetyloxy)methyl]-7-amino-8-oxo-5-thia-1-azabicyclo[4.2.0]oct-2-ene-2-carboxylic acid sodium salt in 35 ml of dimethyl formamide (DMF) is added 2equivalents of p-pivalyloxybenzyl alcohol followed by cooling to 0° C after which 7.2 mM of dicyclohexylcarbodiimide in 7.5 ml of DMF is added dropwise with stirring. The mixture is stirred at 0° C for 1 hour and an additional 4hours at room temperature. The formed dicyclohexylurea is removed by filtration. The filtrate is diluted with chloroform, washed with water, dried over magnesium sulfate, filtered, and evaporated in vacuo to give 3-[(acetyloxy)methyl]-7-amino-8-oxo-5-thia-1-azabicyclo[4.2.0]oct-2-ene-2-carboxylic acid p-pivalyloxybenzyl ester.

When in the above procedure an appropriate amount of p-(propionyloxy) benzyl alcohol, p-(acetyloxy)benzyl alcohol, or p-(valeryloxy)benzyl alcohol is substituted for p-pivalyloxybenzyl alcohol the following respective products are obtained:

3-[(acetyloxy)methyl]-7-amino-8-oxo-5-thia-1-azabicyclo[4.2.0]oct-2-ene-2-carboxylic acid p-(propionyloxy)benzyl ester,
3-[(acetyloxy)methyl]-7-amino-8-oxo-5-thia-1-azabicyclo[4.2.0]oct-2-carboxylic acid p-(acetyloxy)benzyl ester, and 3-[(acetyloxy)methyl]-7-amino-8-oxo-5-thia-1-azabicyclo-[4.2.0]oct-2-ene-2-carboxylic acid p-(valeryloxy)benzyl ester.

EXAMPLE 12

3-[(2-Methyl-1,3,4-thiadiazol-5-ylthio)methyl]-7-amino-8-oxo-5-thia-1-azabicyclo[4,2,0]oct-2-ene-2-carboxylic acid In about 1 liter of water dissolved 0.1 mole of the sodium salt of 3-[(acetyloxy)methyl]-7-amino-8-oxo-5-thia-1-azabicyclo[4.2.0]oct-2-ene-2-carboxylic acid at 70° C under nitrogen atmosphere. To the solution is added 1equivalent of sodium bicarbonate and 2equivalents of 2-methyl-1,3,4-thiadiazol-5-ylthiol. The mixture is stirred at 70° C for 3hours after which the pH is adjusted to 3.5, and the resuslting precipitate collected giving 3-[(2-methyl-1,3,4-thiadiazol-5-ylthio)methyl]-7-amino-8-oxo-5-thia-1-azabicyclo[4.2.0]oct-2-ene-2-carboxylic acid.

When in the above procedure an equivalent amount of 1,3,4-thiadiazol-5-ylthiol, 3-methyl-1,2,4-thiadiazol-5-ylthiol, tetrazol-5-ylthiol, 1-methyltetrazol-5-ylthiol or 2-methyl-1,2,4-oxadiazol-5-ylthiol is substituted for 2-methyl-1,3,4-thiadiazol-5-ylthiol the following respective products are obtained:

3-[(1,3,4-thiadiazol-5-ylthio)methyl]-7-amino-8-oxo-5-thia-1-azabicyclo[4.2.0]oct-2-ene-2-carboxylic acid, When in the procedure of Example 8 an appropriate amount of 3-methyl-7-amino-8-oxo-5-thia-1-azabicyclo[4.2.0]oct-2-ene-2-carboxylic acid is substituted for 3-[(acetyloxy)methyl]-7-amino-8-oxo-5-thia-1-azabicyclo[4.2.0]oct-2-ene-2-carboxylic acid, 3-methyl-7-amino-8-oxo-5-thia-1-azabicyclo[4.2.0]oct-2-ene-2-carboxylic acid pivalyloxymethyl ester is obtained.

EXAMPLE 13

When in the procedure of Example 12 appropriate amounts of the sodium salt of the cephalosporin derivative and the heterocyclicthiol derivative listed below in Table IV are substituted respectively for the sodium salt of 3-[(acetyloxy)methyl]-7-amino-8-oxo-5-thia-1-azabicyclo[4.2.0]oct-2-ene-2-carboxylic acid and 2-methyl-1,3,4-thiadiazol-5-ylthiol the respective products listed in Table IV are obtained.

TABLE IV

| Cephalosporin Derivative | Heterocyclicthiol | Product |
|---|---|---|
| 3-[(acetyloxy)methyl]-7-amino-8-oxo-5-thia-1-azabicyclo[4.2.0]oct-2-ene-2-carboxylic acid propionyloxymethyl ester | 3-methyl-1,2,4-thiadiazol-5-ylthiol | 3-[(3-methyl-1,2,4-thiadiazol-5-ylthio)methyl]-7-amino-8-oxo-5-thia-1-azabicyclo[4.2.0]oct-2-ene-2-carboxylic acid propionyloxymethyl ester |
| 3-[(acetyloxy)methyl]-7-amino-8-oxo-5-thia-1-azabicyclo[4.2.0]oct-2-ene-2-carboxylic acid p-pivalyloxymethyl ester | 1-methyltetrazol-5-ylthiol | 3-[(1-methyltetrazol-5-ylthio)methyl]-7-amino-8-oxo-5-thia-1-azabicyclo-[4.2.0]oct-2-ene-2-carboxylic acid pivalyloxymethyl ester |
| 3-[(acetyloxy)methyl]-7-amino-8-oxo-5-thia-1-azabicyclo[4.2.0]oct-2-ene-2-carboxylic acid acetyloxymethyl ester | 1,3,4-thiadiazol-5-ylthiol | 3-[(1,3,4-thiadiazol-5-ylthio)methyl]-7-amino-8-oxo-5-thia-1-azabicyclo-[4.2.0]oct-2-ene-2-carboxylic acid acetyloxymethyl ester |
| 3-[(acetyloxy)methyl]-7-amino-8-oxo-5-thia-1-azabicyclo[4.2.0]oct-2-ene-2-carboxylic acid butyryloxymethyl ester | tetrazol-5-ylthiol | 3-[(tetrazol-5-ylthio)methyl]-7-amino-8-oxo-5-thia-1-azabicyclo[4.2.0]oct-2-ene-2-carboxylic acid butyryloxymethyl ester |
| 3-[(acetyloxy)methyl]-7-amino-8-oxo-5-thia-1-azabicyclo[4.2.0]oct-2-ene-2-carboxylic acid 2-amino-3-methyl-butyryloxymethyl ester | 2-methyl-1,3,4-oxadiazol-5-ylthiol | 3-[(2-methyl-1,3,4-oxadiazol-5-yl-thio)methyl]-7-amino-8-oxo-5-thia-1-azabicyclo[4.2.0]oct-2-ene-2-carboxylic acid 2-amino-3-methylbutyryloxymethyl ester |
| 3-[(acetyloxy)methyl]-7-amino-8-oxo-5-thia-1-azabicyclo[4.2.0]oct-2-ene-2-carboxylic acid N-ethoxycarbonyl-N-methylaminomethyl ester | 2-methyl-1,3,4-thiadiazol-5-ylthiol | 3-[(2-methyl-1,3,4-thiadiazol-5-yl-thio)methyl]-7-amino-8-oxo-5-thia-1-azabicyclo[4.2.0] oct-2-ene-2-carboxylic acid N-ethoxycarbonyl-N-methylaminomethyl ester |
| 3-[(acetyloxy)methyl]-7-amino-8-oxo-5-thia-1-azabicyclo[4.2.0]oct-2-ene-2-carboxylic acid p-pivalyloxybenzyl ester | 1-methyltetrazol-5-ylthiol | 3-[(1-methyltetrazol-5-ylthio)methyl]-7-amino-8-oxo-5-thia-1-azabicyclo-[4.2.0]oct-2-ene-2-carboxylic acid p-pivalyloxybenzyl ester |
| 3-[(acetyloxy)methyl]-7-amino-7-methoxy-8-oxo-5-thia-1-azabicyclo-[4.2.0]oct-2-ene-2-carboxylic acid (prepared by acid hydrolysis of the corresponding benzhydryl ester described in U.S. patent 3,778,432) | 2-methyl-1,3,4-thiadiazol-5-ylthiol | 3-[(2-methyl-1,3,4-thiadiazol-5-yl-thio)methyl]-7-amino-7-methoxy-8-oxo-5-thia-1-azabicyclo[4.2.0]oct-2-ene-2-carboxylic acid |
| 3-[(acetyloxy)methyl]-7-amino-8-oxo-5-thia-1-azabicyclo[4.2.0]oct-2-ene-2-carboxylic acid p-(propionyloxy)-benzyl ester | -1methyltetrazol-5-ylthiol | 3-[(1-methyltetrazol-5-ylthio)methyl-7-amino-8-oxo-5-thia-1-azabicyclo-[4.2.0]oct-2-ene-2-carboxylic acid p-(propionyloxy)benzyl ester |
| 3-[(acetyloxy)methyl]-7-amino-8-oxo-5-thia-1-azabicyclo[4.2.0]oct-2-ene-2-carboxylic acid p-(acetyloxy)benzyl ester | tetrazol-5-ylthiol | 3-[(tetrazol-5-ylthio)methyl-7-amino-8-oxo-5-thia-1-azabicyclo[4.2.0]oct-2-ene-2-carboxylic acid p-(acetyloxy)-benzyl ester |
| 3-[(acetyloxy)methyl]-7-amino-8-oxo-5-thia-1-azabicyclo[4.2.0]oct-2-ene-2-carboxylic acid p-(valeryloxy)benzyl ester | 3-methyl-1,2,4-thiadiazol-5-ylthiol | 3-[(3-methyl-1,2,4-thiadiazol-5-ylthio)methyl]-7-amino-8-oxo-5-thia-1-azabicyclo[4.2.0]oct-2-ene-2-carboxylic acid p-(valeryoxy)benzyl ester |

3-[(3-methyl-1,2,4-thiadiazol-5-ylthio)methyl]-7-amino-8-oxo-5-thia-1-azabicyclo[4.2.0]oct-2-ene-2-carboxylic acid, 3-[(tetrazol-5-ylthio)methyl]-7-amino-8-oxo-5-thia-1-azabicyclo-[4.2.0]oct-2-ene-2-carboxylic acid, 3-[(1-methyltetrazol-5-ylthio)methyl]-7-amino-8-oxo-5-thia-1-azabicyclo[4.2.0]oct-2-ene-2-carboxylic acid, and 3-[(2-methyl-1,3,4-oxadiazol-5-ylthio)methyl]-7-amino-8-oxo-5-thia-1-azabicyclo[4.2.0]oct-2-ene-2-carboxylic acid.

EXAMPLE 14 p-Azidomethylphenylacetyl chloride

A. A solution of p-chloromethylphenylacetic acid (1.1 g) and sodium azide (2 g) in methanol (50 ml) was refluxed for 3 hours. The solvent was removed under vacuum using a rotary evaporator. The solid residue was dissolved in a mixture of methylene chloride (250 ml) and cold water (50 ml) and slowly acidified with 10% HCl to pH 2-3. The phases were separated, and the aqueous base was extracted twice with methylene chloride (2 × 50 ml). All the organic extracts were combined, dried over sodium sulfate and concentrated under vacuum yielding a white crystalline product which was crystallized from petroleum ether-ether. M.P. 85° C.

B. By stirring a mixture of the thus obtained p-azidomethylphenylacetic acid in thionyl chloride at room temperature for 20 hours the corresponding acid chloride is obtained after removal of the excess reagent under high vacuum at room temperature.

When in the procedure of Example 14 (A) an appropriate amount of an acid listed in the following Table V is substituted for p-chloromethylphenylacetic acid the respective azidomethyl derivatives listed in Table V are obtained:

TABLE V

| ACID DERIVATIVES | AZIDOMETHYL DERIVATIVES |
| --- | --- |
| p-chloromethylhydrotropic acid | p-azidomethylhydrotropic acid |
| p-chloromethylmandelic acid | p-azidomethylmandelic acid |
| p-chloromethyldihydrocynnamic acid | p-azidomethyldihydrocynnamic acid |
| p-chloromethyl-2-methylhydrocynnamic acid | p-azidomethyl-2-methylhydrocynnamic acid |
| 3-(p-chloromethylphenyl)lactic acid | 3-(p-azidomethylphenyl)lactic acid |
| 4-(p-chloromethylphenyl)butyric acid | 4-(p-azidomethylphenyl)butyric acid |
| 2-methyl-4-(p-chloromethylphenyl)butyric acid | 2-methyl-4-(p-azidomethylphenyl)butyric acid |
| 2-hydroxy-4-(p-chloromethylphenyl)butyric acid | 2-hydroxy-4-(p-azidomethylphenyl)butyric acid |
| p-chloromethylphenoxyacetic acid | p-azidomethylphenoxyacetic acid |
| 2-(p-chloromethylphenoxy)propionic acid | 2-(p-azidomethylphenoxy)propionic acid |
| 4-(p-chloromethylphenoxy)butyric acid | 4-(p-azidomethylphenoxy)butyric acid |
| 2-methyl-4-(p-chloromethylphenoxy)butyric acid | 2-methyl-4-(p-azidomethylphenoxy)butyric acid |
| 3-(p-chloromethylphenoxy)propionic acid | 3-(p-azidomethylphenoxy)propionic acid |
| 3-(p-chloromethylphenoxy)lactic acid | 3-(p-azidomethylphenoxy)lactic acid |
| p-chloromethylanilinoacetic acid | p-azidomethylanilinoacetic acid |
| 2-hydroxy-2-[2-(5-chloromethyl)thienyl]acetic acid | 2-hydroxy-2-[2-(5-azidomethyl)thienyl]acetic acid |
| 2-(p-chloromethyl)anilinopropionic acid | 2-(p-azidomethyl)anilinopropionic acid |
| 4-(p-chloromethylanilino)butyric acid | 4-(p-azidomethylanilino)butyric acid |
| 3-(p-chloromethylanilino)butyric acid | 3-(p-azidomethylanilino)butyric acid |
| p-chloromethylphenylthioacetic acid | p-azidomethylphenylthioacetic acid |
| 2-(p-chloromethylphenyl)thiopropionic acid | 2-(p-azidomethylphenyl)thiopropionic acid |
| 4-(p-chloromethylphenyl)thiobutyric acid | 4-(p-azidomethylphenyl)thiobutyric acid |
| o-chloro-p-chloromethylphenylacetic acid | o-chloro-p-azidomethylphenylacetic acid |
| p-chloromethylphenylglycine hydrochloride | p-azidomethylphenylglycine hydrochloride |
| p-(chloromethylphenyl)alanine hydrochloride | p-(azidomethylphenyl)alanine hydrochloride |
| 2-amino-4-(p-chloromethylphenyl)butyric acid hydrochloride | 2-amino-4-(p-azidomethylphenyl)butyric acid hydrochloride |
| 2-amino-4-(p-chloromethylphenoxy)butyric acid hydrochloride | 2-amino-4-(p-azidomethylphenoxy)butyric acid hydrochloride |
| 3-(p-chloromethylphenoxy)alanine hydrochloride | 3-(p-azidomethylphenoxy)alanine hydrochloride |
| 2-amino-4-(p-chloromethylanilino)butyric acid hydrochloride | 2-amino-4-(p-azidomethylanilino)butyric acid hydrochloride |
| 2-amino-4-(p-chloromethylphenyl)thiobutyric acid hydrochloride | 2-amino-4-(p-azidomethylphenyl)thiobutyric acid hydrochloride |
| 3-(p-chloromethylphenyl)thioalanine hydrochloride | 3-(p-azidomethylphenyl)thioalanine hydrochloride |
| 2-[2-(5-chloromethyl)thienyl]glycine hydrochloride | 2-[2-(5-azidomethyl)thienyl]glycine hydrochloride |
| 2-amino-3-[2-(5-chloromethyl)thienyl]propionic acid hydrochloride | 2-amino-3-[2-(5-azidomethyl)thienyl]propionic acid hydrochloride |
| 2-amino-4-[2-(5-chloromethyl)thienyl]butyric acid hydrochloride | 2-amino-4-[2-(5-azidomethyl)thienyl]butyric acid hydrochloride |
| p-chloromethylphenylmalonic acid | p-azidomethylphenylmalonic acid |
| 2-sulfo-p-chloromethylphenylacetic acid | 2-sulfo-p-azidomethylphenylacetic acid |
| 3-(p-chloromethylphenyl)-2-sulfopropionic acid | 3-(p-azidomethylphenyl)-2-sulfopropionic acid |
| 4-(p-chloromethylphenyl)-2-sulfobutyric acid | 4-(p-azidomethylphenyl)-2-sulfobutyric acid |
| p-chloromethylbenzylmalonic acid | p-azidomethylbenzylmalonic acid |
| p-chloromethylphenethylmalonic acid | p-azidomethylphenethylmalonic acid |
| 2-(p-chloromethylphenoxy)ethylmalonic acid | 2-(p-azidomethylphenoxy)ethylmalonic acid |
| 2-(p-chloromethylphenyl)thioethylmalonic acid | 2-(p-azidomethylphenyl)thioethylmalonic acid |
| p-chloromethylanilinomethylmalonic acid | p-azidomethylanilinomethylmalonic acid |
| 2-[2-(5-chloromethyl)thienyl]malonic acid | 2-[2-(5-azidomethyl)thienyl]malonic acid |
| 2-[2-(5-chloromethyl)thenyl]malonic acid | 2-[2-(5-azidomethyl)thenyl]malonic acid |

EXAMPLE 15

3-[(Acetyloxy)methyl]-7-[[2-[4-(azidomethyl)phenyl]acetyl]amino]-8-oxo-5-thia-1-azabicyclo[4.2.0]oct-2-ene-2-carboxylic acid A mixture of p-azidomethylphenylacetyl chloride (1.38 g) and 3-[(acetyloxy)methyl]-7-amino-8-oxo-5-thia-1-azabicyclo[4.2.0]oct-2-ene-2-carboxylic acid (1.38 g) in 250 ml of ethyl acetate was refluxed for 45 minutes. The solvent was removed under vacuum at 35° C yielding a solid residue which was purified by chromatography using 200 g of silica gel eluting with benzene-acetone to give 3-[(acetyloxy)methyl]-7-[[2-[4-(azidomethyl)phenyl]acetyl]amino]-8-oxo-5-thia-1-azabicyclo[4.2.0]oct-2-ene-2-carboxylic acid. M.P. 135°-136° C.

When in the procedure of Example 15 an appropriate amount of an acid chloide listed in the following Table VI is substituted for p-azidomethylphenylacetyl chloride the corresponding cephalosporin derivative listed in Table VI is obtained. The acid chloride derivatives listed in the following Table VI are obtained from the corresponding acid listed in Table V by treatment with thionyl chloride by the general procedure described in Example 14 (B).

TABLE VI

| ACID CHLORIDE | CEPHALOSPORIN DERIVATIVE |
| --- | --- |
| p-azidomethylhydrotropic acid chloride | 3-[(acetyloxy)methyl]-7-[[2-[4-(azidomethyl)phenyl]-2-methylacetyl]amino]-8-oxo-5-thia-1-azabicyclo[4.2.0]oct-2-ene-2-carboxylic acid |
| p-azidomethyldihydrocynnamic acid chloride | 3-[(acetyloxy)methyl]-7-[[3-[4-(azidomethyl)phenyl]propionyl]amino]-8-oxo-5-thia-1-azabicyclo[4.2.0]oct-2-ene-2-carboxylic acid |
| p-azidomethyl-2-methylhydrocynnamic acid | 3-[(acetyloxy)methyl]-7-[[3-[4-(azidomethyl)phenyl]-2-methylpropionyl]amino]-8-oxo-5-thia-1-azabicyclo[4.2.0]oct-2-ene-2-carboxylic acid |
| 4-(p-azidomethylphenyl)butyric acid chloride | 3-[(acetyloxy)methyl]-7-[[4-[4-(azidomethyl)phenyl]butyryl]amino]-8-oxo-5-thia-1-azabicyclo[4.2.0]oct-2-ene-2-carboxylic acid |
| 2-methyl-4-(p-azidomethylphenyl)butyric acid | 3-[(acetyloxy)methyl]-7-[[4-[4-(azidomethyl)phenyl]-2- |

TABLE VI-continued

| ACID CHLORIDE | CEPHALOSPORIN DERIVATIVE |
|---|---|
| chloride | methylbutyryl]amino]-8-oxo-5-thia-1-azabicyclo[4.2.0]-oct-2-ene-2-carboxylic acid |
| p-azidomethylphenoxy-acetic acid chloride | 3-[(acetyloxy)methyl]-7-[[2-[4-(azidomethyl)phenoxy]-acetyl]amino]-8-oxo-5-thia-1-azabicyclo[4.2.0]oct-2-ene-2-carboxylic acid |
| 2-(p-azidomethylphenoxy)-propionic acid chloride | 3-[(acetyloxy)methyl]-7-[[2-[4-(azidomethyl)phenoxy]-2-methylacetyl]amino]-8-oxo-5-thia-1-azabicyclo[4.2.0]-oct-2-ene-2-carboxylic acid |
| 4-(p-azidomethylphenoxy)-butyric acid chloride | 3-[(acetyloxy)methyl]-7-[[4-[4-(azidomethyl)phenyl]butyryl]amino]-8-oxo-5-thia-1-azabicyclo[4.2.0]oct-2-ene-2-carboxylic acid |
| 2-methyl-4-(p-azidomethylphenoxy)butyric acid chloride | 3-[(acetyloxy)methyl]-7-[[4-[4-(azidomethyl)phenoxy]-2-methylbutyryl]amino]-8-oxo-5-thia-1-azabicyclo[4.2.0]-oct-2-ene-2-carboxylic acid |
| 3-(p-azidomethylphenoxy)-propionic acid | 3-[(acetyloxy)methyl]-7-[[3-[4-(azidomethyl)phenoxy]propionyl]amino]-8-oxo-5-thia-1-azabicyclo[4.2.0]oct-2-ene-2-carboxylic acid |
| p-azidomethylanilinoacetic acid chloride | 3-[(acetyloxy)methyl]-7-[[2-[4-(azidomethyl)anilino]acetyl]amino]-8-oxo-5-thia-1-azabicyclo[4.2.0]oct-2-ene-2-carboxylic acid |
| 2-(p-azidomethyl)anilino-propionic acid chloride | 3-[(acetyloxy)methyl]-7-[[2-[4-(azidomethyl)anilino]-2-methylacetyl]amino]-8-oxo-5-thia-1-azabicyclo[4.2.0]-oct-2-ene-2-carboxylic acid |
| 4-(p-azidomethylanilino)-butyric acid chloride | 3-[(acetyloxy)methyl]-7-[[4-[4-(azidomethyl)anilino]butyryl]amino]-8-oxo-5-thia-1-azabicyclo[4.2.0]oct-2-ene-2-carboxylic acid |
| 3-(p-azidomethylanilino)-butyric acid chloride | 3-[(acetyloxy)methyl]-7-[[3-[4-(azidomethyl)anilino]-2-methylpropionyl]amino]-8-oxo-5-thia-1-azabicyclo[4.2.0]oct-2-ene-2-carboxylic acid |
| p-azidomethylphenylthio-acetic acid chloride | 3-[(acetyloxy)methyl]-7-[[2-[4-(azidomethyl)phenylthio]-acetyl]amino]-8-oxo-5-thia-1-azabicyclo[4.2.0]oct-2-ene-2-carboxylic acid |
| 2-(p-azidomethylphenyl)-thiopropionic acid chloride | 3-[(acetyloxy)methyl]-7-[[2-[4-(azidomethyl)phenylthio]-2-methylacetyl]amino]-8-oxo-5-thia-1-azabicyclo[4.2.0]-oct-2-ene-2-carboxylic acid |
| 4-(p-azidomethylphenyl)-thiobutyric acid chloride | 3-[(acetyloxy)methyl]-7-[[4-[4-(azidomethyl)phenylthio]-butyryl]amino]-8-oxo-5-thia-1-azabicyclo[4.2.0]oct-2-ene-2-carboxylic acid |
| o-chloro-p-azidomethyl-phenylacetic acid chloride | 3-[(acetyloxy)methyl]-7-[[2-[2-(chloro)-4-(azidomethyl)-phenyl]acetyl]amino]-8-oxo-5-thia-1-azabicyclo[4.2.0]-oct-2-ene-2-carboxylic acid |
| 5-azidomethyl-2-thienyl-acetyl chloride | 3-[(acetyloxy)methyl]-7-[[2-[5-(azidomethyl)-2-thienyl]-acetyl]amino]-8-oxo-5-thia-1-azabicyclo[4.2.0]oct-2-ene-2-carboxylic acid |
| 2-azidomethyl-4-methoxy-mandelic acid chloride | 3-[(acetyloxy)methyl]-7-[[2-[2-(azidomethyl)]-4-methoxy-phenyl]-2-hydroxyacetyl]-amino]-8-oxo-5-thia-1-azabicyclo[4.2.0]oct-2-ene-2-carboxylic acid |
| p-azidomethylmandelic acid chloride | 3-[(acetyloxy)methyl]-7-[[2-[4-(azidomethyl)phenyl]-2-hydroxyacetyl]amino]-8-oxo-5-thia-1-azabicyclo[4.2.0]-oct-2-ene-2-carboxylic acid |
| 2-(p-azidomethylphenyl)-lactic acid chloride | 3-[(acetyloxy)methyl]-7-[[3-[4-(azidomethyl)phenyl]-2-hydroxypropionyl]amino]-8-oxo-5-thia-1-azabicyclo[4.2.0]oct-2-ene-2-carboxylic acid |
| 2-hydroxy-4-(p-azido-methylphenyl)butyric acid chloride | 3-[(acetyloxy)methyl]-7-[[4-[4-(azidomethyl)phenyl]-2-hydroxybutyryl]amino]-8-oxo-5-thia-1-azabicyclo[4.2.0]-oct-2-ene-2-carboxylic acid |
| 3-(p-azidomethylphenoxy)-lactic acid chloride | 3-[(acetyloxy)methyl]-7-[[3-[4-(azidomethyl)phenoxy]-2-hydroxypropionyl]amino]-8-oxo-5-thia-1-azabicyclo[4.2.0]oct-2-ene-2-carboxylic acid |
| 2-hydroxy-2-[2-(5-azido-methyl)thienyl]acetic acid chloride | 3-[(acetyloxy)methyl]-7-[[2-[5-(azidomethyl)-2-thienyl]-2-hydroxyacetyl]amino]-8-oxo-5-thia-1-azabicyclo[4.2.0]-oct-2-ene-2-carboxylic acid |

EXAMPLE 16

7-[[2-[4-(Azidomethyl)phenyl]acetyl]amino]-3-methyl-8-oxo-5-thia-1-azabicyclo[4.2.0]oct-2-ene-2-carboxylic acid A mixture of p-azidomethylphenylacetyl chloride (0.6 g) and 7-amino-3-methyl-8-oxo-5-thia-1-azabicyclo[4.2.0]oct-2-ene-2-carboxylic acid (0.6 g) in 250 ml of ethyl acetate was refluxed for 50 minutes after which the solvent was removed under vacuum yielding an oily residue which was purified by chromatography using 60 g of silica gel and benzene-acetone as the eluant to give 7-[[2-[4-(azidomethyl)phenyl]acetyl]amino]-3-methyl-8-oxo-5-thia-1-azabicyclo[4.2.0]oct-2-ene-2-carboxylic acid. M.P. 154°–155° C.

EXAMPLE 17

3-[(Acetyloxy)methyl]-7-[[2-[4-(azidomethyl)phenyl]-2-aminoacetyl]amino]-8-oxo-5-thia-1-azabicyclo[4.2.0]-oct-2-ene-2-carboxylic acid p-Azidomethylphenylglycine wherein the amino group is protected with tert-butoxycarbonyl is treated with isobutyl chloroformate in the presence of triethylamine. Equimolar amounts of the thus obtained mixed anhydride and the triethylamine salt of 3-[(acetyloxy)-methyl]-7-amino-8-oxo-5-thia-1-azabicyclo[4.2.0]oct-2ene-2carboxylic acid are reacted at 0° C for about 4 hours. The resulting product is isolated and the amine protecting group is removed by acid hydrolysis to give 3-[(acetyloxy)methyl]-7-[[2-[4-(azidomethyl)phenyl]-2-aminoacetyl]amino]-8-oxo-5-thia-1-azabicyclo[4.2.0]-oct-2-ene-2-carboxylic acid.

When an appropriate amount of the amino acid listed in the following Table VII is substituted for p-azidomethylphenylglycine in the above Example 17 the corresponding cephalosporin derivative listed in the following Table VII is obtained.

TABLE VII

| ACID DERIVATIVE | CEPHALOSPORIN DERIVATIVE |
|---|---|
| 3-(p-azidomethylphenyl)-alanine | 3-[(acetyloxy)methyl]-7-[[3-[4-(azidomethyl)phenyl]-2-aminopropionyl]amino]-8-oxo-5-thia-1-azabicyclo[4.2.0]-oct-2-ene-2-carboxylic acid |
| 2-amino-4-(p-azidomethyl-phenyl)butyric acid | 3-[(acetyloxy)methyl]-7-[[4-[4-(azidomethyl)phenyl]-2-aminobutyryl]amino]-8-oxo-5-thia-1-azabicyclo[4.2.0]-oct-2-ene-2-carboxylic acid |
| 2-amino-4-(p-azidomethyl-phenoxy)butyric acid | 3-[(acetyloxy)methyl]-7-[[4-[4-(azidomethyl)phenoxy]-2-aminobutyryl]amino]-8-oxo-5-thia-1-azabicyclo[4.2.0]oct- |

TABLE VII-continued

| ACID DERIVATIVE | CEPHALOSPORIN DERIVATIVE |
|---|---|
| 3-(p-azidomethylphenoxy)-alanine | 3-[(acetyloxy)methyl]-7-[[3-[4-(azidomethyl)phenoxy]-2-aminopropyl]amino]-8-oxo-5-thia-1-azabicyclo[4.2.0]-oct-2-ene-2-carboxylic acid |
| 2-amino-4-(p-azidomethyl-anilino)butyric acid | 3-[(acetyloxy)methyl]-7-[[4-[4-(azidomethyl)anilino]-2-aminobutyryl]amino]-8-oxo-5-thia-1-azabicyclo[4.2.0]-oct-2-ene-2-carboxylic acid |
| 2-amino-4-(p-azidomethyl-phenyl)thiobutyric acid | 3-[(acetyloxy)methyl]-7-[[4-[4-(azidomethyl)phenylthio]-2-aminobutyryl]amino]-8-oxo-5-thia-1-azabicyclo[4.2.0]-oct-2-ene-2-carboxylic acid |
| 3-(p-azidomethylphenyl)-thioalanine | 3-[(acetyloxy)methyl]-7-[[3-[4-(azidomethyl)phenylthio]-2-aminopropionyl]amino]-8-oxo-5-thia-1-azabicyclo-[4.2.0]oct-2-ene-2-carboxylic acid |
| 2-[2-(5-azidomethyl)thienyl]glycine | 3-[(acetyloxy)methyl]-7-[[2-[5-(azidomethyl)-2-thienyl]-2-aminoacetyl]amino]-8-oxo-5-thia-1-azabicyclo[4.2.0]-oct-2-ene-2-carboxylic acid |
| 2-amino-3-[2-(5-azido-methyl)thienyl]propionic acid | 3-[(acetyloxy)methyl]-7-[[3-[5-(azidomethyl)-2-thienyl]-2-aminopropionyl]amino]-8-oxo-5-thia-1-azabicyclo-[4.2.0]oct-2-ene-2-carboxylic acid |
| 2-amino-4-[2-(5-azido-methyl)thienyl]butyric acid | 3-[(acetyloxy)methyl]-7-[[4-[5-(azidomethyl)-2-thienyl]-2-aminobutyryl]amino]-8-oxo-5-thia-1-azabicyclo[4.2.0]-oct-2-ene-2-carboxylic acid |

EXAMPLE 18

3-[(Acetyloxy)methyl]-7-[[2-[4-(azidomethyl)phenyl]-2-carboxyacetyl]amino]-8-oxo-5-thia-1-azabicyclo[4.2.0]-oct-2-ene-2-carboxylic acid α-Carboxy-p-azidomethylphenylacetyl nitrophenyl polymer, prepared according to the procedure described in Canadian Pat. No. 892,580, carrying 4 m. mole of p-azidomethylphenylmalonic acid was suspended for 8 hours in 20 ml of dry methylene chloride solution containing 1 m. mole of 3-[(acetyloxy)methyl]-7-amino-8-oxo-5-thia-1-azabicyclo[4.2.0]-oct-2-ene-2-carboxylic acid triethylammonium salt, which is prepared from 544 mg of 7-aminocephalosporanic acid (1 m. mole) and 0.56 ml of triethylamine (1 m. mole) at room temperature. After only traces of 7-aminocephalosporanic acid remain in solution, which is determined by thin layer chromatography on cellulose in 70% aqueous propanol, the polymer was filtered off and washed with 3 portions of 5- ml each of methylene chloride. The combined filtrates were evaporated and the residue was dissolved in 20 ml of distilled water. This solution was acidified to pH 2 by adding 0.2 normal hydrochloric acid and extracted with ethyl acetate. The organic solution was dried over sodium sulfate and evaporated at room temperature. The remaining soldi was dried overnight over phosphorus pentoxide under vacuum to give 3-[(acetyloxy)methyl]-7-[[2-[4-(azidomethyl)phenyl]-2-carboxyacetyl]amino]-8-oxo-5-thia-1-azabicyclo[4.2.0]oct-2-ene-2-carboxylic acid.

When in the procedure of Example 18 an appropriate amount of an acid listed in the following Table VIII is substituted for p-azidomethylphenylmalonic acid the respective cephalosporin derivatives listed in Table VIII are obtained:

TABLE VIII

| ACID | CEPHALOLOSPORIN DERIVATIVE |
|---|---|
| 2-sulfo-p-azidomethylphenyl-acetic acid | 3-[(acetyloxy)methyl]-7-[[2-[4-(azidomethyl)phenyl]-2-sulfoacetyl]amino]-8-oxo-5-thia-1-azabicyclo[4.2.0]oct-2-ene-2-carboxylic acid |
| 4-(p-azidomethylphenyl)-2-sulfobutyric acid | 3-[(acetyloxy)methyl]-7-[[4-[4-(azidomethyl)phenyl]-2-sulfobutyryl]amino]-8-oxo-5-thia-1-azabicyclo[4.2.0]oct-2-ene-2-carboxylic acid |
| p-azidomethylbenzyl-malonic acid | 3-[(acetyloxy)methyl]-7-[[3-[4-(azidomethyl)phenyl]-2-carboxypropionyl]amino]-8-oxo-5-thia-1-azabicyclo-[4.2.0]oct-2-ene-2-carboxylic acid |
| 2-(p-azidomethylphenoxy)-ethylmalonic acid | 3-[(acetyloxy)methyl]-7-[[4-[4-(azidomethyl)phenoxy)]-2-carboxybutyryl]amino]-8-oxo-5-thia-1-azabicyclo[4.2.0]-oct-2-ene-2-carboxylic acid |
| 2-(p-azidomethylphenyl)thio-ethylmalonic acid | 3-[(acetyloxy)methyl]-7-[[4-[4-(azidomethyl)phenylthio]-2-carboxybutyryl]amino]-8-oxo-5-thia-1-azabicyclo-[4.2.0]oct-2-ene-2-carboxylic acid |
| -p-azidomethylanilinomethyl-malonic acid | 3-[(acetyloxy)methyl]-7-[[3-[4-(azidomethyl)anilino]-2-carboxypropionyl]amino]-8-oxo-5-thia-1-azabicyclo-[4.2.0]oct-2-ene-2-carboxylic acid |
| 2-[2-(5-azidomethyl)thienyl]-malonic acid | 3-[(acetyloxy)methyl]-7-[[3-[5-(azidomethyl)-2-thienyl]-2-carboxypropionyl]amino]-8-oxo-5-thia-1-azabicyclo-[4.2.0]oct-2-ene-2-carboxylic acid |

When in the procedue of Example 15 an appropriate amount of an acid chloride listed in the following Table IX is substituted for p-azidomethylphenylacetyl chloride and an appropriate amount of a 7-aminocephalosporin derivative listed in the following Table IX is substituted for 3-[(acetyloxy)methyl]-7-amino-8-oxo-5-thia-1-azabicyclo[4.2.0]oct-2-ene-2-carboxylic acid the corresponding cephalosporin product listed in Table IX is obtained. The acid chloride derivatives are obtained from the corresponding acid as described in Example 14.

TABLE IX

| ACID CHLORIDE | 7-AMINOCEPHALOSPORIN DERIVATIVE | CEPHALOSPORIN PRODUCT |
|---|---|---|
| p-azidomethylphenyl-acetyl chloride | 3-[(acetyloxy)methyl]-7-amino-7-methoxy-8-oxo-5-thia-1-azabicyclo[4.2.0]oct-2-ene-2-carboxylic acid | 3-[(acetyloxy)methyl]-7-[[2-[4-(azidomethyl)phenyl]-acetyl]amino]-7-methoxy-8-oxo-5-thia-1-azabicyclo[4.2.0]-oct-2-ene-2-carboxylic acid |
| p-azidomethylhydrotropic acid chloride | 3-[(2-methyl-1,3,4-thiadiazol-5-ylthio)methyl]-7-amino-7-methoxy-8-oxo-5-thia-1-azabicyclo[4.2.0]oct-2-ene-2-carboxylic acid | 7-[[2-[4-(azidomethyl)phenyl]-2-methylacetyl]amino]-7-methoxy-3-[(2-methyl-1,3,4-thiadiazol-5-ylthio)methyl]-8-oxo-5-thia-1-azabicyclo[4.2.0]oct-2-ene-2-carboxylic acid |
| p-azidomethyl-2-methyl-hydrocynnamic acid | 3-[(1-methyltetrazol-5-ylthio)methyl]-7-amino-8-oxo-5-thia-1-azabicyclo[4.2.0]-oct-2-ene-2-carboxylic acid p-pivalyloxy- | 7-[[3-[4-(azidomethyl)phenyl]-2-methylpropionyl]amino]-3-[(1-methyltetrazol-5-ylthio)- |

TABLE IX-continued

| ACID CHLORIDE | 7-AMINOCEPHALOSPORIN DERIVATIVE | CEPHALOSPORIN PRODUCT |
| --- | --- | --- |
| | benzyl ester | methyl]-8-oxo-5-thia-1-azabi-cyclo[4.2.0]oct-2-ene-2-carboxylic acid |
| p-azidomethylphenoxyacetic acid chloride | 3-[(2-methyl-1,3,4-oxadiazol-5-ylthio)-methyl]-7-amino-8-oxo-5-thia-1-azabi-cyclo[4.2.0]oct-2-ene-2-carboxylic acid 2-amino-3-methylbutyryloxymethyl ester | 7-[[2-[4-(azidomethyl)phenoxy]-acetyl]amino]-3-[(2-methyl-1,-3,4-oxadiazol-5-ylthio)methyl]-8-oxo-5-thia-1-azabicyclo-[4.2.0]oct-2-ene-2-carboxylic acid 2-amino-3-methylbutyryl-oxymethyl ester |
| 2-methyl-4-(p-azidomethyl-phenoxy)butyric acid chloride | 3-[(1-methyltetrazol-5-ylthio)methyl]-7-amino-8-oxo-5-thia-1-azabicyclo[4.2.0]-oct-2-ene-2-carboxylic acid pivaloxy-methyl ester | 7-[[4-[4-(azidomethyl)phenoxy]-2-methylbutyryl]amino]-3-[(1-methyltetrazol-5-ylthio)methyl]-8-oxo-5-thia-1-azabicyclo[4.2.0]-oct-2-ene-2-carboxylic acid pivalyloxymethyl ester |
| p-azidomethylanilino-acetic acid chloride | 3-[(2-methyl-1,3,4-thiadiazol-5-ylthio)-methyl]-7-amino-8-oxo-5-thia-1-azabicyclo-[4.2.0]oct-2-ene-2-carboxylic acid | 7-[[2-[4-(azidomethyl)anilino]-acetyl]amino]-3-[(2-methyl-1-3,4-thiadiazol-5-ylthio)methyl]-8-oxo-5-thia-1-azabicyclo[4.2.0]-oct-2-ene-2-carboxylic acid |
| 5-azidomethyl-2-thienyl-acetyl chloride | 3-[(acetyloxy)methyl]-7-amino-8-oxo-5-thia-1-azabicyclo[4.2.0]oct-2-ene-2-carboxylic acid p-pivalyloxybenzyl ester | 3-[(acetyloxy)methyl]-7-[[2-[5-(azidomethyl)-2-thienyl]acetyl]-amino -8-oxo-5-thia-1-azabicy-clo[4.2.0]oct-2-ene-2-carboxylic acid p-pivalyloxybenzyl ester |
| 3-(p-azidomethylphenyl)-lactic acid chloride | 3-[(acetyloxy)methyl]-7-amino-8-oxo-5-thia-1-azabicyclo[4.2.0]oct-2-ene-2-carboxylic acid N-ethoxycarbonyl-N-methylaminomethyl ester | 3[(acetyloxy)methyl]-7-[[3-[4-(azidomethyl)phenyl]-2-hydroxy-propionyl]amino]-8-oxo-5-thia-1-azabicyclo[4.2.0]oct-2-ene-2-carboxylic acid N-ethoxycarbon-yl-N-methylaminomethyl ester |
| 2-azidomethyl-4-methoxy-mandelic acid chloride | 3-[(acetyloxy)methyl]-7-amino-8-oxo-5-thia-1-azabicyclo[4.2.0]oct-2-ene-2-carboxylic acid 2-amino-3-methylbutyryl-oxymethyl ester | 3-[(acetyloxy)methyl]-7-[[2-[2-(azidomethyl)-4-methoxyphenyl]-2-hydroxyacetyl]amino]-8-oxo-5-thia-1-azabicyclo[4.2.0]oct-2-ene-2-carboxylic acid 2-amino-3-methylbutyryloxymethyl ester |
| o-chloro-p-azidomethyl-phenylacetic acid chloride | 3-[(acetyloxy)methyl]-7-amino-8-oxo-5-thia-1-azabicyclo[4.2.0]oct-2-ene-2-carboxylic acid pivalyloxymethyl ester | 3-[(acetyloxy)methyl]-7-[[2-[2-(chloro)-4-(azidomethyl)phenyl]-acetyl]amino]-8-oxo-5-thia-1-azabicyclo[4.2.0]oct-2-ene-2-carboxylic acid pivalyloxymethyl ester |
| p-azidomethylphenylacetyl chloride | 3-[(1-methyltetrazol-5-ylthio)methyl]-7-amino-8-oxo-5-thia-1-azabicyclo[4.2.0]-oct-2-ene-2-carboxylic acid | 7-[[2-[4-(azidomethyl)phenyl]-acetyl]amino]-3-[(1-methyltet-razol-5-ylthio)methyl]-8-oxo-5-thia-1-azabicyclo[4.2.0]oct-2-ene-2-carboxylic acid |
| p-azidomethylphenylacetyl chloride | 3-[(tetrazol-5-ylthio)methyl]-7-amino-8-oxo-5-thia-1-azabicyclo[4.2.0]oct-2-ene-2-carboxylic acid | 7-[[2-[4-(azidomethyl)phenyl]-acetyl]amino]-3-[(tetrazol-5-ylthio)methyl]-8-oxo-5-thia-1-azabicyclo[4.2.0]oct-2-ene-2-carboxylic acid |

When in the procedure of Example 17 an appropriate amount of an amine protected amino acid listed in the following Table X is substituted for p-azidomethyl-phenylglycine and an appropriate amount of a cephalosporin derivative listed in the following Table X is substituted for 3-[(acetyloxy)methyl]-7-amino-8-oxo-5-thia-1-azabicyclo[4.2.0]oct-2-ene-2-carboxylic acid the corresponding cephalosporin product listed in Table X is obtained.

TABLE X

| AMINO ACID | 7-AMINOCEPHALOSPORIN DERIVATIVE | CEPHALOSPORIN PRODUCT |
| --- | --- | --- |
| 3-(p-azidomethylphenyl)-alanine | 3-[(acetyloxy)methyl]-7-amino-8-oxo-5-thia-1-azabicyclo[4.2.0]oct-2-ene-2-carboxylic acid pivalyloxymethyl ester | 3-[(acetyloxy)methyl]-7-[[3-[4-(azidomethyl)phenyl]-2-aminopropionyl]amino]-8-oxo-5-thia-1-azabicyclo[4.2.0]oct-2-ene-2-carboxylic acid pivalyloxymethyl ester |
| 2-amino-4-(p-azidomethylphenoxy)butyric acid | 3-[(acetyloxy)methyl]-7-amino-8-oxo-5-thia-1-azabicyclo[4.2.0]oct-2-ene-2-carboxylic acid N-methyl-N-propionylaminomethyl ester | 3-[(acetyloxy)methyl]-7-[[4-[4-(azidomethyl)phenoxy]-2-aminobutyryl]amino]-8-oxo-5-thia-1-azabicyclo[4.2.0]oct-2-ene-2-carboxylic acid N-methyl-N-propionylaminomethyl ester |
| 2-amino-4-(p-azidomethylanilino)butyric acid | 3-[(2-methyl-1,3,4-thiadiazol-5-ylthio)methyl]-7-amino-8-oxo-5-thia-1-azabicyclo[4.2.0]oct-2-ene-2-carboxylic acid | 7-[[4-[4-(azidomethy)anilino]-2-aminobutyryl]amino]-3-[(2-methyl-1,3,4-thiadiazol-5-ylthio)methyl]-8-oxo-5-thia-1-azabicyclo[4.2.0]oct-2-ene-2-carboxylic acid |
| 3-(p-azidomethylphenyl)-thioalanine | 3-[(acetyloxy)methyl]-7-amino-7-methoxy-8-oxo-5-thia-1-azabicyclo[4.2.0]oct-2-ene-2-carboxylic acid | 3-[(acetyloxy)methyl]-7-[[3-[4-(azidomethyl)phenylthio]-2-aminopropionyl]amino]-7-methoxy-8-oxo-5-thia-1-azabicyclo[4.2.0]oct-2-ene-2-carboxylic acid |
| 2-amino-3-[2-(5-azidomethyl)thienyl]propionic acid | 3-[(tetrazol-5-ylthio)methyl]-7-amino-8-oxo-5-thia-1-azabicyclo[4.2.0]oct-2-ene-2-carboxylic acid p-acetyloxy)benzyl ester | 7-[[3-[5-(azidomethyl)-2-thienyl]-2-aminopropionyl]amino]-3-[(tetrazol-5-ylthio)methyl]-8-oxo-5-thia-1-azabicyclo[4.2.0]oct-2-ene-2-carboxylic acid p-(acetyloxy)benzyl ester |
| p-azidomethylphenylglycine | 3-[(1-methyltetrazol-5-ylthio)methyl]-7-amino-8-oxo-5-thia-1-azabicyclo[4.2.0]oct-2-ene-2-carboxylic acid | 7-[[2-[4-(azidomethyl)phenyl]-2-aminoacetyl]amino]-3-[1-methyltetrazol-5-ylthio)methyl]-8-oxo-5-thia-1-azabicyclo[4.2.0]oct-2-ene-2-carboxylic acid |
| p-azidomethylphenylglycine | 3-methyl-7-amino-8-oxo-5-thia-1-azabicyclo[4.2.0]oct-2-ene-2-carboxylic acid | 7-[[2-[4-(azidomethyl)phenyl]-2-aminoacetyl]amino]-3-methyl-8-oxo-5-thia-1-azabicyclo[4.2.0]oct-2-ene-2-carboxylic acid |
| p-azidomethylphenylglycine | 3-methyl-7-amino-8-oxo-5-thia-1-azabicyclo[4.2.0]oct-2-ene-2-carboxylic acid pivalyloxymethyl ester | 7-[[2-[4-(azidomethyl)phenyl]-2-aminoacetyl]amino]-3-methyl-8-oxo-5-thia-1-azabicyclo[4.2.0]oct-2-ene-2-carboxylic acid pivalyloxymethyl ester |

When in the procedure of Example 18 an appropriate amount of the acid derivative listed in the following Table XI is substituted for p-azidomethylphenylmalonic acid and an appropriate amount of a 7-aminocephalosporin derivative listed in the following Table XI is substituted for 3-[(acetyloxy)methyl]-7-amino-8-oxo-5-thia-1-azabicyclo[4.2.0]oct-2-ene-2-carboxylic acid the corresponding cephalosporin product listed in the following Table Xl is obtained.

TABLE XI

| ACID DERIVATIVE | 7-AMINOCEPHALOSPORIN DERIVATIVE | CEPHALOSPORIN PRODUCT |
| --- | --- | --- |
| 2-sulfo-p-azidomethylphenylacetic acid | 3-[(acetyloxy)methyl]-7-amino-8-oxo-5-thia-1-azabicyclo[4.2.0]oct-2-ene-2-carboxylic acid propionyloxymethyl ester | 3-[(acetyloxy)methyl]-7-[[2-[4-(azidomethyl)phenyl]-2-sulfoacetyl]amino]-8-oxo-5-thia-1-azabicyclo[4.2.0]oct-2-ene-2-carboxylic acid propionyloxymethyl ester |
| p-azidomethylbenzylmalonic acid | 3-[(acetyloxy)methyl]-7-amino-8-oxo-5-thia-1-azabicyclo[4.2.0]oct-2-ene-2-carboxylic acid N-acetylaminomethyl ester | 3-[(acetyloxy)methyl]-7-[[3-[4-(azidomethyl)phenyl]-2-carboxypropionyl]amino]-8-oxo-5-thia-1-azabicyclo[4.2.0]oct-2-ene-2-carboxylic acid N-acetylaminoethyl ester |
| 2-(p-azidomethylphenoxy)ethylmalonic acid | 3-[(acetyloxy)methyl]-7-amino-8-oxo-5-thia-1-azabicyclo[4.2.0]oct-2-ene-2-carboxylic acid p-(valaryloxy)benzyl ester | 3-[(acetyloxy)methyl]-7-[[4-[4-(azidomethyl)phenoxy]-2-carboxybutyryl]amino]-8-oxo-5-thia-1-azabicyclo[4.2.0]oct-2-ene-2-carboxylic acid p-(valaryloxy)benzyl ester |
| p-azidomethylanilinomethylmalonic acid | 3-[(1-methyltetrazol-5-ylthio)methyl]-7-amino-8-oxo-5-thia-1-azabicyclo[4.2.0]oct-2-ene-2-carboxylic acid | 7-[[3-[4-(azidomethyl)anilino]-2-carboxypropionyl]amino]-3-[(1-methyltetrazol-5-ylthio)methyl]-8-oxo-5-thia-1-azabicyclo[4.2.0]oct-2-ene-2-carboxylic acid |
| p-azidomethylphenylmalonic acid | 3-[(acetyloxy)methyl]-7-amino-7-methoxy-8-oxo-5-thia-1-azabicyclo[4.2.0]-oct-2-ene-2-carboxylic acid | 3-[(acetyloxy)methyl]-7-[[2-[4-(azidomethyl)phenyl]-2-carboxyacetyl]amino]-7-methoxy-8-oxo-5-thia-1-azabicyclo[4.2.0]oct-2-ene-2-carboxylic acid |
| 2-[2-(5-azidomethylthenyl]malonic acid | 3-[(3-methyl-1,2,4-thiadiazol-5-ylthio)methyl]-7-amino-8-oxo-5-thia-1-azabicyclo[4.2.0]oct-2-ene-2-carboxylic acid propionyloxymethyl ester | 7-[[3-[5-(azidomethyl)-2-thienyl]-2-carboxypropionyl]amino]-3-[(3-methyl-1,2,4-thiadiazol-5-ylthio)methyl]-8-oxo-5-thia-1-azabicyclo[4.2.0]oct-2-ene-2-carboxylic acid pro- |

| ACID DERIVATIVE | 7-AMINOCEPHALOSPORIN DERIVATIVE | CEPHALOSPORIN PRODUCT |
|---|---|---|
| | | pionyloxymethyl ester |

TABLE XI-continued

EXAMPLE 19

3-[(Acetyloxy)methyl]-7-[[2-[4-(azidomethyl)phenyl]-acetyl]amino]-8-oxo-5-thia-1-azabicyclo[4.2.0]oct-2-ene-2-carboxylic acid A. A mixture of 1 g. of 3-[(acetyloxy)methyl]-7-amino-8-oxo-5-thia-1-azabicyclo[4.2.0]oct-2-ene-2-carboxylic acid and 1 g of p-chloromethylphenylacetyl chloride in 45 ml of ethylacetate is refluxed for about 2 hours after which the solvent is removed under vacuum yielding a yellow-brown amorphous product which is chromatographed on silica gel using benzene-acetone as the eluant to give 3-[(acetyloxy)methyl]-7-[[2-[4-(chloromethyl)phenyl]acetyl]amino]-8-oxo-5-thia-1-azabicyclo[4.2.0]oct-2-ene-2-carboxylic acid. M.P. 164°-165° C. (dec.).

B. A warm solution of 1 g of 3-[(acetyloxy)methyl]-7-[[2-[4-(chloromethyl)phenyl]acetyl]amino]-8-oxo-5-thia-1-azabicyclo[4.2.0]-oct-2-ene-2-carboxylic acid and 2 g. of sodium azide in 80 ml of methanol was refluxed for 4 hours after which the solvent was removed under high vacuum at room temperature. The residue was triturated with 80 ml of benzeneacetone (2:1) to give 3-[(Acetyloxy)methyl]-7-[[2-[4-(azidomethyl)phenyl]-acetyl]amino]-8-oxo-5-thia-1-azabicyclo[4.2.0]oct-2-ene-2carboxylic acid. M.P. 135°-136° C.

In a similar manner other compounds of the invention may be prepared by coupling an appropriate halomethyl substituted acid listed in Table I, Table II, Table III and Examples 2, 3, 4, 6 and 7 with appropriate 7-aminocephalosporin derivatives as disclosed herein followed by treatment with zodium azide as in the procedure of Example 19.

EXAMPLE 20

3-[(Acetyloxy)methyl]-7-[[2-[4-(azidomethyl)phenyl]-acetyl]amino]-8-oxo-5-thia-1-azabicyclo[4.2.0]oct-2-ene-2-carboxylic acid N-ethoxycarbonyl-N-methylaminomethyl ester A mixture of 1.2 g of the sodium salt of 3-[(acetyloxy)-methyl]-7-[[2-[4-(azidomethyl)phenyl]acetyl]amino]-8-oxo-5-thia-1-azabicyclo[4.2.0]oct-2-ene-2-carboxylic acid and 0.5 g of N-chloromethyl-N-methylurethane in 40 ml of dimethylformamide is stirred at room temperature for 2 hours. The mixture is poured into ice-water and decanted. The oily residue is taken up in 75 ml of ethyl acetate and washed with 5 ml of dilute aqueous sodium bicarbonate and 15 ml of water then dried over magnesium sulfate, filtered and evaporated to give 3-[(acetyloxy)methyl]-7-[[2-(4-(azidomethyl)phenyl]-acetyl]amino]-8-oxo-5-thia-1-azabicyclo[4.2.0]oct-2-ene-2-carboxylic acid N-ethoxycarbonyl-N-methylaminoethyl ester.

EXAMPLE 21

3-[(Acetyloxy)methyl]-7-[[2-[4-(azidomethyl)phenyl]-acetyl]amino]-8-oxo-5-thia-1-azabicyclo[4.2.0]oct-2-ene-2-carboxylic acid p-pivalyloxybenzyl ester To a solutin of 1.8 of 3-[(acetyloxy)methyl]-7-[[2-[4-(azidomethyl)phenyl]acetyl]amino]-8-oxo-5-thia-1-azabicyclo[4.2.0]oct-2-ene-2-carboxylic acid hydrochloride in 25 ml of dimethyl formamide is added 0.78 g of p-pivalyloxybenzyl alcohol followed by cooling to 0° C after which 3.7 mole of dicyclohexylcarbodiimide in 7.5 ml of dimethyl formamide is added dropwise with stirring. The reaction mixture is stirred for 1 hour at 0° C and for an additional 4 hours at room temperature. The formed dicyclohexylurea is removed by filtration. The filtrate is diluted with chloroform and washed with water. The organic layer is then dried over magnesium sulfate filtered and evaporated in vacuo to give an oil which is triturated with ether to give 3-[(acetyloxy)methyl]-7-[[2-[4-(azidomethyl)phenyl]acetyl]amino]-8-oxo-5-thia-1-azabicyclo[4.2.0]oct-2-ene-2-carboxylic acid p-pivalyloxybenzyl ester.

EXAMPLE 22

3-[(Acetyloxy)methyl]-7-[[2-[4-(azidomethyl)phenyl]-2-(5-indanyloxycarbonyl)acetyl]amino]-8-oxo-5-thia-1-azabicyclo-[4.2.0]oct-2-ene-2-carboxylic acid To 25.3 m mole of 3-[(acetyloxy)methyl]-7-[[2-[4-(azidomethyl)phenyl]-2-carboxyacetyl]amino]-8-oxo-5-thia-1-azabicyclo[4.2.0]oct-2-ene-2-carboxylic acid in 35 ml dioxane is added 6N hydrochloric acid to give a pH of 2.5. Then 24.1 m moles N,N'-dicyclohexylcarbodiimide in 35 ml dioxane is added and the mixture is stirred at room temperature for 15 to 20 minutes followed by the addition of 24.1 m moles of 5-indanol. The mixture is stirred for 4 hours. The formed N,N'-dicyclohexylurea is removed by filtration and the filtrate is extracted 3 times with methyl isobutyl ketone. The organic extract is washed with water, dried over magnesium sulfate and concentrated to dryness in vacuo to yield 3-[(acetyloxy)methyl]-7-[[2-[4-(azidomethyl)-phenyl]-2-(5-indanyloxycarbonyl)acetyl]amino]-8-oxo-5-thia-1-azabicyclo[4.2.0]oct-2-ene-2-carboxylic acid.

EXAMPLE 23

3-[(2-Methyl-1,3,4-thiadiazol-5-ylthio)methyl]-7-[[2-[4-(azidomethyl)phenyl]acetyl]aminio]-8-oxo-5-thia-1-azabicyclo[4.2.0]oct-2-ene-2-carboxylic A solution of 3mM of 3-[(acetyloxy)methyl]-7-[[2-[4-(azidomethyl)phenyl]acetyl]amino]-8-oxo-5-thia-1-azabicyclo[4.2.0]oct-2-ene-2-carboxylic acid in 100 ml of water is treated with 3 mM of sodium bicarbonate and 6 mM of 2-methyl-1,3,4-thiadiazol-5-ylthio at 70° C under nitrogen for 3½ hours. The water is removed in vacuo and the residue is taken up in methanol. A large excess of acetonitrile is added to precipitate the product which is isloated by filtration and dried in a vacuum desiccator to give 3-[(2-methyl-1,3,4-thiadiazol-5-ylthio)methyl]-7-[[2-[4-(azidomethyl)phenyl]-acetyl]amino]-8-oxo-5-thia-1-azabicyclo[4.2.0]oct-2-ene-2-carboxylic acid.

Similarly, other compounds of the invention wherein the 3-position of the cephalosporin ring is substituted with a heterocyclicthiomethyl group may be prepared from the corresponding 3-[(acetyloxy)methyl]-substituted cephalosporin compound by reaction with an appropriate heterocyclicthiol derivative as described herein.

We claim:

1. A compound selected from a base of the formula

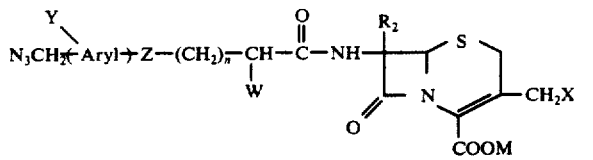

wherein Aryl is selected from phenyl and 2-thienyl; Y is selected from hydrogen, chlorine, bromine, a straight or branched lower alkyl group of from 1 to 4 carbon atoms and a lower alkoxy group of from 1 to 4 carbon atoms with the proviso that when Aryl is 2-thienyl, Y is hydrogen; Z is selected from a bond, oxygen, sulfur and imino with provisio that when Aryl is 2-thienyl, Z is a bond; W is selected from hydrogen, methyl, amino, hydroxy, $SO_3H$ and $COOR_1$ wherein $R_1$ is selected from hydrogen and 5-indanyl; $n$ is zero, 1 or 2 with the proviso that when W is other than hydrogen or methyl and Z is other than a bond, $n$ is not zero; $R_2$ is selected from hydrogen, and methoxy; M is selected from hydrogen; a pharmaceutically acceptable non-toxic cation; alkanoyloxymethyl wherein the alkanoyl moiety contains from 1 to 5 carbon atoms and may be straight or branched; alkanoylaminomethyl wherein the alkanoyl moitety contains from 1 to 5 carbon atoms and may be straight or branched and wherein the amino nitrogen atom may be substituted with an alkyl group of from 1 to 4 carbon atoms; alkoxycarbonylaminomethyl wherein the alkoxy moitey contains from 1 to 4 carbon atoms and may be straight or branched and wherein the amino nitrogen atom may be substituted with an alkyl group of from 1 to 4 carbon atoms; p-(alkanoyloxy)benzyl wherein the alkanoyl moiety contains from 1 to 5 carbon atoms and may be straight or branched; and aminoalkanoyloxymethyl wherein the alkanoyl moiety contains from 2 to 15 carbon atoms and the amino nitrogen may be mono- or di-substituted with a lower alkyl group of from 1 to 4 carbon atoms; X is hydrogen or acetoxy; and pharmaceutically acceptable salts thereof.

2. A compound of claim 1 wherein Aryl is phenyl.
3. A compound of claim 2 wherein $R_2$ is in the cis-position.
4. A compound of claim 1 wherein Aryl is 2-thienyl.
5. A compound of claim 4 wherein $R_2$ is in the cis-position.
6. A compound of claim 1 wherein W is hydrogen.
7. A compound of claim 6 wherein Z is a bond.
8. A compound of claim 6 wherein Z is oxygen or sulfur.
9. A compound of claim 6 wherein Z is imino.
10. A compound of claim 1 wherein W is methyl.
11. A compound of claim 10 wherein Z is a bond.
12. A compound of claim 10 wherein Z is oxygen or sulfur.
13. A compound of claim 10 wherein Z is imino.
14. A compound of claim 1 wherein W is hydroxy.
15. A compound of claim 14 wherein Z is a bond.
16. A compound of claim 14 wherein Z is oxygen or sulfur.
17. A compound of claim 14 wherein Z is imino.
18. A compound of claim 1 wherein W is amino.
19. A compound of claim 18 wherein Z is a bond.
20. A compound of claim 18 wherein Z is oxygen or sulfur.
21. A compound of claim 18 wherein Z is imino.
22. A compound of claim 1 wherein W is $COOR_1$ or $SO_3H$.
23. A compound of claim 22 wherein Z is a bond.
24. A compound of claim 22 wherein Z is oxygen or sulfur.
25. A compound of claim 22 wherein Z is imino.
26. A compound selected from a base of the formula:

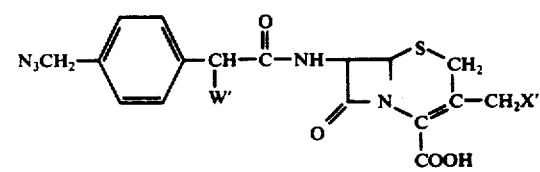

wherein W' is selected from hydrogen, hydroxy, amino, COOH and $SO_3H$; X' is hydrogen or acetoxy; and wherein the hydrogen atoms at the 6- and 7-positions are cis to one another; and pharmaceutically acceptable salts thereof.

27. A compound of claim 26 which is 3-[(acetyloxy)-methyl]-7-[[2-[4-(azidomethyl)phenyl]acetyl]amino]-8-oxo-5-thia-1-azabicyclo[4.2.0]oct-2-ene-2-carboxylic acid and pharmaceutically acceptable salts thereof.

28. A compound of claim 26 which is 3-[(acetyloxy)-methyl]-7-[[2-[4-(azidomethyl)phenyl]-2-hydroxyacetyl]amino]-8-oxo-5-thia-1-azabicyclo[4.2.0]oct-2-ene-2-carboxylic acid and pharmaceutically acceptable salts thereof.

29. A compound of claim 26 which is 3-[(acetyloxy)-methyl]-7-[[2-[4-(azidomethyl)phenyl]-2-aminoacetyl]-amino]-8-oxo-5-thia-1-azabicyclo[4.2.0]oct-2-ene-2-carboxylic acid and pharmaceutically acceptable salts thereof.

30. A compound of claim 26 which is 3-[(acetyloxy)-methyl]-7-[[2-[4-(azidomethyl)phenyl]-2-carboxyacetyl]amino]-8-oxo-5-thia-1-azabicyclo[4.2.0]oct-2-ene-2-carboxylic acid and pharmaceutically acceptable salts thereof.

31. A compound of claim 26 which is 3-[(acetyloxy)-methyl]-7-[[2-[4-(azidomethyl)phenyl]-2-sulfoacetyl]-amino]-8-oxo-5-thia-1-azabicyclo[4.2.0]oct-2-ene-2-carboxylic acid and pharmaceutically acceptable salts thereof.

32. A compound of claim 26 which is 3-methyl-7-[[2-[4-(azidometyl)phenyl]-2-aminoacetyl]amino]-8-oxo-5-thia-1-azabicyclo[4.2.0]oct-2-ene-2-carboxylic acid and pharmaceutically acceptable salts thereof.

* * * * *